US009439958B2

(12) United States Patent
Arntzen et al.

(10) Patent No.: US 9,439,958 B2
(45) Date of Patent: Sep. 13, 2016

(54) STABILIZED VIRUS LIKE PARTICLES HAVING ENHANCED MUCOSAL IMMUNOGENICITY

(75) Inventors: Charles J. Arntzen, Gold Canyon, AZ (US); Melissa Herbst-Kralovetz, Phoenix, AZ (US)

(73) Assignee: ARIZONA BOARD OF REGENTS ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 13/518,504

(22) PCT Filed: Dec. 23, 2010

(86) PCT No.: PCT/US2010/061993
§ 371 (c)(1),
(2), (4) Date: Nov. 8, 2012

(87) PCT Pub. No.: WO2011/079260
PCT Pub. Date: Jun. 30, 2011

(65) Prior Publication Data
US 2013/0095134 A1    Apr. 18, 2013

Related U.S. Application Data

(60) Provisional application No. 61/289,737, filed on Dec. 23, 2009.

(51) Int. Cl.
| | | |
|---|---|---|
| A61K 39/12 | (2006.01) | |
| C12N 7/00 | (2006.01) | |
| A61K 9/00 | (2006.01) | |
| A61K 9/16 | (2006.01) | |
| A61K 39/125 | (2006.01) | |
| A61K 39/00 | (2006.01) | |

(52) U.S. Cl.
CPC .............. *A61K 39/12* (2013.01); *A61K 9/0043* (2013.01); *A61K 9/1652* (2013.01); *A61K 9/1694* (2013.01); *A61K 39/125* (2013.01); *C12N 7/00* (2013.01); *A61K 39/00* (2013.01); *A61K 2039/5258* (2013.01); *A61K 2039/53* (2013.01); *A61K 2039/542* (2013.01); *A61K 2039/543* (2013.01); *C12N 2770/16023* (2013.01); *C12N 2770/16034* (2013.01); *C12N 2770/16051* (2013.01)

(58) Field of Classification Search
CPC .............. A61K 2300/00; A61K 39/12; A61K 2039/5258; A61K 2039/53; A61K 39/00; A61K 39/39; A61K 2800/412; A61K 2039/543; A61K 2039/55555; A61K 39/125; A61K 8/97; A61K 9/10; A61K 2039/545; A61K 2039/55583; A61K 2039/57; A61K 2039/542; A61K 9/0043; A61K 9/0053; C07K 14/005; C07K 14/08; C07K 2319/735; C12N 2770/16034; C12N 2770/16023; C12N 2770/16022; C12N 15/86; C12N 2770/1605
See application file for complete search history.

(56) References Cited

U.S. PATENT DOCUMENTS

| | | | | |
|---|---|---|---|---|
| 5,068,109 A | * | 11/1991 | Foldager et al. | 424/441 |
| 5,106,616 A | * | 4/1992 | McAnalley et al. | 424/85.2 |
| 5,118,673 A | * | 6/1992 | Carpenter et al. | 514/54 |
| 5,308,838 A | * | 5/1994 | McAnalley et al. | 424/278.1 |
| 5,409,703 A | * | 4/1995 | McAnalley et al. | 424/435 |
| 5,760,102 A | * | 6/1998 | Hall et al. | 523/120 |
| 5,902,796 A | * | 5/1999 | Shand et al. | 514/54 |
| 5,925,357 A | * | 7/1999 | Cerqueira et al. | 424/744 |
| 5,929,051 A | * | 7/1999 | Ni et al. | 514/54 |
| 6,251,678 B1 | * | 6/2001 | Volkin et al. | 436/8 |
| 6,777,000 B2 | | 8/2004 | Ni et al. | |
| 7,481,997 B1 | * | 1/2009 | Hardy | 424/93.1 |
| 7,494,669 B2 | * | 2/2009 | Ni et al. | 424/488 |
| 7,879,338 B2 | * | 2/2011 | Hamilton et al. | 424/216.1 |
| 7,955,603 B2 | * | 6/2011 | Richardson et al. | 424/204.1 |
| 2003/0175370 A1 | * | 9/2003 | Yates et al. | 424/744 |
| 2003/0220485 A1 | * | 11/2003 | Ni et al. | 536/2 |
| 2005/0084534 A1 | * | 4/2005 | Ni et al. | 424/488 |
| 2005/0155113 A1 | * | 7/2005 | Hamilton et al. | 800/288 |
| 2006/0211653 A1 | * | 9/2006 | Ni et al. | 514/54 |
| 2007/0298052 A1 | | 12/2007 | Mayeresse | |
| 2010/0278846 A1 | * | 11/2010 | Ferguson | 424/184.1 |
| 2012/0121710 A1 | * | 5/2012 | Herbst-Kralovetz et al. | 424/489 |

FOREIGN PATENT DOCUMENTS

| | | | |
|---|---|---|---|
| WO | 2008042789 A1 | 4/2008 | |
| WO | WO 2008042789 A1 * | 4/2008 | |
| WO | WO 2009039229 A2 * | 3/2009 | ............. A61K 39/12 |

OTHER PUBLICATIONS

The Centers for Disease Control and Prevention (CDC). "Prevent the Spread of Norovirus." www_cdc_gov/features/norovirus/. Jul. 29, 2013.*
The Centers for Disease Control and Prevention (CDC). "Norovirus: CDC Clinical Overview." Feb. 21, 2013.*
Shirato H, Ogawa S, Ito H, Sato T, Kameyama A, Narimatsu H, Xiaofan Z, Miyamura T, Wakita T, Ishii K, Takeda N. Noroviruses distinguish between type 1 and type 2 histo-blood group antigens for binding. J Virol. Nov. 2008;82(21):10756-67. Epub Aug. 13, 2008.*

(Continued)

*Primary Examiner* — Rachel B Gill
(74) *Attorney, Agent, or Firm* — George A. Leone; Citadel Patent Law

(57) ABSTRACT

A method of producing an immune response in a subject including the step of administering to the subject a dry powder vaccine composition having a dry powder containing a subunit antigen with virus-like particles, where the subunit antigen is stabilized by a polysaccharide-containing plant extract, and where mucosal vaccination results in an immune response which is not further enhanced by co-inclusion of adjuvants.

6 Claims, 12 Drawing Sheets

(56) References Cited

OTHER PUBLICATIONS

Figure 1A:
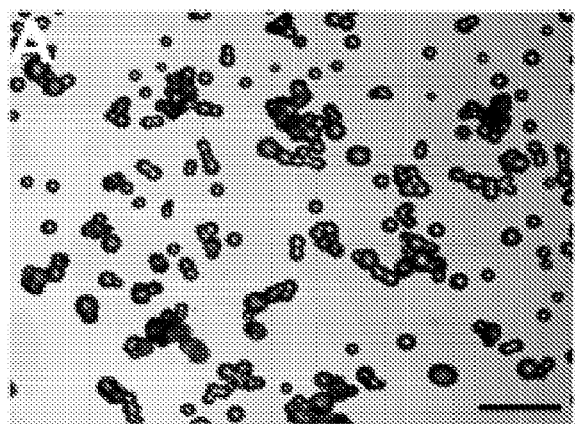

Velasquez LS, Shira S, Berta AN, Kilbourne J, Medi BM, Tizard I, Ni Y, Arntzen CJ, Herbst-Kralovetz MM. Intranasal delivery of Norwalk virus-like particles formulated in an in situ gelling, dry powder vaccine. Vaccine. Jul. 18, 2011;29(32):5221-31. Epub Jun. 2, 2011.*

Debbaudt, A., Zalba, M., Ferreira, M. L. and Gschaider, M. E. (2001), Theoretical and Experimental Study of Pb2+ and Hg2+ Adsorption on Biopolymers, 2. Experimental Part. Macromol. Biosci., 1: 249-257.*

Aw TG, Gin KY, Ean Oon LL, Chen EX, Woo CH. Prevalence and genotypes of human noroviruses in tropical urban surface waters and clinical samples in Singapore. Appl Environ Microbiol. Aug. 2009;75(15):4984-92. doi: 10.1128/AEM.00489-09. Epub Jun. 12, 2009.*

Maunula L, Miettinen IT, von Bonsdorff CH. Norovirus outbreaks from drinking water. Emerg Infect Dis. Nov. 2005;11(11):1716-21.*

"Nastech to Evaluate GelSite Polymer for Enhancement of Intranasal Delivery." GENNewsHighlights. Genetic Engineering & Biotechnology News. Online. Apr. 10, 2007.*

Donaldson EF, Lindesmith LC, Lobue AD, Baric RS. Viral shape-shifting: norovirus evasion of the human immune system. Nat Rev Microbiol. Mar. 2010;8(3):231-41. Epub Feb. 2, 2010.*

The Plant List (2010). Version 1. Published on the Internet; http://www.theplantlist.org/browse/A/Asparagaceae/Aloe/; Accessed Oct. 4, 2013.*

CSL™ Seasonal Influenza Vaccine package insert. 2013-2014.*

Surjushe A, Vasani R, Sable DG. Aloe vera: a short review. Indian J Dermatol. 2008;53(4):163-6.*

Talwar GP, Dar SA, Rai MK, Reddy KV, Mitra D, Kulkarni SV, Doncel GF, Buck CB, Schiller JT, Muralidhar S, Bala M, Agrawal SS, Bansal K, Verma JK. A novel polyherbal microbicide with inhibitory effect on bacterial, fungal and viral genital pathogens. Int J Antimicrob Agents. Aug. 2008;32(2):1 80-5. Epub Jun. 20, 2008.*

Gauntt CJ, Wood HJ, McDaniel HR, McAnalley BH. Aloe polymannose enhances anti-coxsackievirus antibody titres in mice. Phytother Res. Jun. 2000;14(4):261-6.*

Moghaddasi SM, et.al. Int J Biol Med Res. 2011; 2(1): 466-471.* www.nanotherapeutics.com/gelvac/. "GELVAC™/Gelsite®." Accessed Feb. 12, 2015.*

Turner CE, Williamson DA, Stroud PA, Talley DJ. Evaluation and comparison of commercially available Aloe vera L. products using size exclusion chromatography with refractive index and multi-angle laser light scattering detection. Int Immunopharmacol. Dec. 20, 2004;4(14)1 727-37.*

Weeratna RD, Makinen SR, McCluskie MJ, Davis HL. TLR agonists as vaccine adjuvants: comparison of CpG ODN and Resiquimod (R-848). Vaccine. Nov. 1, 2005;23(45):5263-70. Epub Jul. 18, 2005.*

BusinessWire. "Nanotherapeutics Acquires Assets of DelSite." http://www.businesswire.com/news/home/20091001005281/en/Nanotherapeutics-Acquires-Assets-DelSite#.Vc-OZPIdVDB. Pub. Online Oct. 1, 2009.*

Berens KL, Sullivan TR. Advances in Intranasal Therapeutics—Delivery of Dry Powder Pharmaceuticals and Biologics. Aug. 9, 2007. http://mysticpharmaceuticals.com/AdvancesIntranasal-TherapeuticsSpecialReport.pdf.*

Huang J, Garmise RJ, Crowder TM, Mar K, Hwang CR, Hickey AJ, Mikszta JA, Sullivan VJ. A novel dry powder influenza vaccine and intranasal delivery technology: induction of systemic and mucosal immune responses in rats. Vaccine. Dec. 21, 2004;23(6):794-801.*

Hickey AJ, Garmise RJ. Dry powder nasal vaccines as an alternative to needle-based delivery. Crit Rev Ther Drug Carrier Syst. 2009;26(1)1-27.*

Turner CE, Williamson DA, Stroud PA, Talley DJ. Evaluation and comparison of commercially available Aloe vera L. products using size exclusion chromatography with refractive index and multi-angle laser light scattering detection. Int Immunopharmacol. Dec. 20, 2004;4(14):1727-37.*

Steenkamp V, Stewart MJ. Medicinal applications and toxicological activities of Aloe products. Pharm. Biol. 2007, 45, 411-420.*

McConaughy SD, Kirkland SE, Treat NJ, Stroud PA, McCormick CL. Tailoring the network properties of Ca2+ crosslinked Aloe vera polysaccharide hydrogels for in situ release of therapeutic agents. Biomacromolecules. Nov. 2008;9(11):3277-87. Epub Oct. 21, 2008.*

Hamman JH. Composition and applications of Aloe vera leaf gel. Molecules. Aug. 8, 2008;13(8):1599-616.*

Alpar, H. Oya, et al., "Biodegradable mucoadhesive particulates for nasal and pulmonary antigen and DNA delivery," Adv. Drug Deliv. Rev., Jan. 2005, pp. 411-430, vol. 57, No. 3.

Baldwin, Susan L, et al., "Intradermal immunization improves protective efficacy of a novel TB vaccine candidate," Vaccine, May 2009, pp. 3063-3071, vol. 27, No. 23.

Ball, Judith M., et al., "Oral Immunization with Recombinant Norwalk Virus-Like Particles Induces a Systemic and Mucosal Immune Response in Mice," J. Virol., Feb. 1998, pp. 1345-1353, vol. 72, No. 2.

Ball, Judith M., et al., "Recombinant Norwalk Virus-Like Particles Given Orally to Volunteers: Phase I Study," Gastroenterology, Jul. 1999, pp. 40-48, vol. 117, No. 1.

Balmelli, Carole, et al., "Nasal immunization of mice with human papillomavirus type 16 virus-like particles elicits neutralizing antibodies in mucosal secretions," J. Virol., Oct. 1998, pp. 8220-29, vol. 72, No. 10.

Belshe, Robert B., et al., "The efficacy of live attenuated, cold-adapted, trivalent, intranasal influenzavirus vaccine in children," N. Engl. J. Med., May 1998, pp. 1405-1412, vol. 338, No. 20.

Bernstein, David I., et al., "Effect of imiquimod as an adjuvant for immunotherapy of genital HSV in guinea-pigs," Vaccine, Jan. 1995, pp. 72-76, vol. 13, No. 1.

Bernstein, David I., et al., "Daily or weekly therapy with resiquimod (R-848) reduces genital recurrences in herpes simplex virus-infected guinea pigs during and after treatment," J. Infect. Dis., Mar. 2001, pp. 844-849, vol. 183, No. 6.

Buonaguro, L., et al., "Induction of systemic and mucosal cross-Glade neutralizing antibodies in BALB/c mice immunized with human immunodeficiency virus type 1 Glade A virus-like particles administered by different routes of inoculation," J. Virol., Jun. 2005, pp. 7059-7067, vol. 79, No. 11.

Canessa, C., et al., "The immunity of upper airways," Int. J. Immunopathol. Pharmacol., Jan.-Mar. 2010, pp. 8-12, vol. 23, Supp. 1.

Chadwick, Sandra, et al., "Delivery strategies to enhance mucosal vaccination," Expert Opin. Biol. Ther., Apr. 2009, pp. 427-440, vol. 9, No. 4.

Davis, S.S., "Nasal vaccines," Adv. Drug Deliv. Rev., Sep. 2001, pp. 21-42, vol. 51, Nos. 1-3.

El-Kamary, Samer S., et al., "Adjuvanted intranasal norwalk virus-like particle vaccine elicits antibodies and antibody-secreting cells that express homing receptors for mucosal and peripheral lymphoid tissues," J. Infect. Dis., Dec. 2010, pp. 1649-1658, vol. 202, No. 11.

Estes, Mary K., et al., "Norwalk virus vaccines: challenges and progress," J. Infect. Dis., May 2000, pp. S367-S373, vol. 181, Supp. 2.

Fraillery, Dominique, et al., "Rectal and vaginal immunization of mice with human papillomavirus L1 virus-like particles," Vaccine, Apr. 2009, pp. 2326-2334, vol. 27, No. 17.

Garg, Neeraj K., et al., "Mucosal delivery of vaccines: role of mucoadhesive/biodegradable polymers," Recent Pat. Drug Deliv. Formul., Jun. 1, 2010, pp. 114-128, vol. 4, No. 2.

Garmise, Robert J., et al., "Novel dry powder preparations of whole inactivated influenza virus for nasal vaccination," AAPS PharmSciTech, 2007, p. E81, vol. 8, No. 4.

Geysen, H. Mario, et al., "Use of peptide synthesis to probe viral antigens for epitopes to a resolution of a single amino acid," Proc. Natl. Acad. Sci., Jul. 1984, pp. 398-4002, vol. 81.

Glass, Roger I., et al., "Norovirus gastroenteritis," N. Engl. J. Med., Oct. 2009, pp. 1776-1785, vol. 361.

(56) References Cited

OTHER PUBLICATIONS

Graham, B.S., et al., "Mucosal delivery fo human papillomavirus pseudovirus-encasidated plasmids improves the potency of DNA vaccination," Mucosal Immunol., Jun. 2010, pp. 475-486, vol. 3, No. 5.
Green, Kim Y., et al., "Comparison of the reactivities of baculovirus-expressed recombinant Norwalk virus capsid antigen with those of the native Norwalk virus antigen in serologic assays and some epidemiologic observations," J. Clin. Microbiol., Aug. 1993, pp. 2185-2191, vol. 31, No. 8.
Guerrero, Roberto A., et al., "Recombinant Norwalk Virus-Like Particles Administered Intranasally to Mice Induce Systemic and Mucosal (Fecal and Vaginal) Immune Responses," J. Virol., Oct. 2001, pp. 9713-9722, vol. 75, No. 20.
Hefferon, Kathleen Laura, "The Mucosal Immune Response to Plant-Derived Vaccines," Pharm. Res., Oct. 2010, pp. 2040-2042, vol. 27, No. 10.
Herbst-Kralovetz, Melissa, et al., "Norwalk virus-like particles as vaccines," Expert Rev. Vaccines, Mar. 2010, pp. 299-307, vol. 9, No. 3.
Hickey, Anthony J., et al., "Dry powder nasal vaccines as an alternative to needle-based delivery," Crit. Rev. Ther. Drug Carrier Syst., 2009, pp. 1-27, vol. 26, No. 1.
Holmgren, Jan, et al., "Mucosal immunity and vaccines." Nat. Med., Apr. 2005, pp. S45-S53, vol. 11, Supp.
Holmgren, Jan, et al., "Mucosal adjuvants and anti-infection and anti-immunopathology vaccines based on cholera toxin, cholera toxin B subunit and CpG DNA," Expert Rev. Vaccines, Apr. 2003, pp. 205-217, vol. 2. No. 2.
Huang, Juan, et al., "A novel dry powder influenza vaccine and intranasal delivery technology: induction of systemic and mucosal immune responses in rats," Vaccine, Dec. 2004, pp. 794-801, vol. 23, No. 6.
Huang, Zhong, et al., "Virus-like particle expression and assembly in plants: hepatitis B and Norwalk viruses," Vaccine, Mar. 2005, pp. 1851-1858, vol. 23, No. 15.
Inskeep, Tiffany K., et al., Oral vaccine formulations stimulate mucosal and systemic antibody responses against staphylococcal entertoxin B using a piglet model, Clin. Vaccine Immunol., Jun. 2010, pp. 1163-1169, vol. 17, No. 8.
Jiang, Xi, et al., "Expression, Self-Assembly, and Antigenicity of the Norwalk Virus Capsid Protein," J. Virol., Nov. 1992, pp. 6527-6532, vol. 66, No. 1.
Jiang, Lingmin, et al., "The application of mucoadhesive polymers in nasal drug delivery," Drug Dev. Ind. Pharm., Mar. 2010, pp. 323-336, vol. 36, No. 3.
Kuolee, Rhonda, et al., "M cell-targeted delivery of vaccines and therapeutics," Expert Opin. Drug Deilv., Jun. 2008, pp. 693-702, vol. 5, No. 6.
Lanza, Silvia R., et al., "Simian recombinant adenovirus delivered by the mucosal route modulates gammadelta T cells from murine genital tract," Vaccine, Jun. 2010, pp. 4600-4608, vol. 28, No. 29.
Lorin, M.I., et al., "Quantitative composition of nasal secretions in normal subjects," J. Lab Clin. Med., Aug. 1972, pp. 275-281, vol. 80, No. 2.
Ma, Yifan, et al., "Assessing the immunopotency of Toll-like receptor agonists in an in vitro tissue-engineered immunological model," Immunology, Jul. 2010, pp. 374-387, vol. 130, No. 3.
Mason, Hugh S., et al., "Expression of Norwalk virus capsid protein in transgenic tobacco and potato and its oral immunogenicity in mice," Proc. Natl. Acad. Sci., May 1996, pp. 5335-5340, vol. 93, No. 11.
Mestecky, Jiri, "The common mucosal immune system and current strategies for induction of immune responses in external secretions," J. Clin. Immunol., Jul. 1987, pp. 265-276, vol. 7, No. 4.
Nardelli-Haefliger, Denise, et al., "Mucosal but not parenteral immunization with purified human papillomavirus type 16 virus-like particles induces neutralizing titers of antibodies throughout the estrous cycle of mice," J. Virol., Nov. 1999, pp. 9609-9613, vol. 73, No. 11.
Nichol, Kristin L., et al., "Effectiveness of live, attenuated intranasal influenza virus vaccine in healthy, working adults: a randomized controlled trial," JAMA, Jul. 1999, pp. 137-44, vol. 282, No. 2.
Noda, Kenji, et al., "Nasal vaccination with P6 outer membrane protein and alpha-galactosylceramide induces nontypeable Haemophilus influenzae-specific protective immunity associated with NKT cell activation and dendritic cell expansion in nasopharynx," Vaccine, May 2010, pp. 5068-5074, vol. 28, No. 31.
Patel, Manish M., et al., "Noroviruses: a comprehensive review," J. Clin. Virol., Jan. 2009, pp. 1-8, vol. 44, No. 1.
Patel, Manish M., et al., "Systematic literature review of role of noroviruses in sporadic gastroenteritis," Emerg. Infect. Dis., Aug. 2008, pp. 1224-1231, vol. 14, No. 8.
Pawar, Dilip, et al., "Evaluation of mucoadhesive PLGA microparticles for nasal immunization," AAPS J., Jun. 2010, pp. 130-137, vol. 12, No. 2.
Reeck, Amanda, et al., "Serological correlate of protection against norovirus-induced gastroenteritis," J. Infect. Dis., Oct. 2010, pp. 1212-1218, vol. 202, No. 8.
Saluja, V., et al., "A comparison between spray drying and spray freeze drying to produce an influenza subunit vaccine powder for inhalation," J. Control. Release, Jun. 2010, pp. 127-133, vol. 144, No. 2.
Santi, Luca, et al., "An efficient plant viral expression system generating orally immunogenic Norwalk virus-like particles," Vaccine, Mar. 2008, pp. 1846-1854, vol. 26, No. 15.
Tacket, Carol O., et al., "Human immune responses to a novel norwalk virus vaccine delivered in transgenic potatoes," J. Infect. Dis., Jul. 2000, pp. 302-305, vol. 182, No. 1.
Tafaghodi, Mohsen, et al., "Preparation and in vivo study of dry powder microspheres for nasal immunization," J. Drug Target., Apr. 2010, pp. 235-242, vol. 18, No. 3.
Tosh, Pritish K., et al., "Emerging vaccines for influenza," Expert Opin. Emerg. Drugs, Mar. 2008, pp. 21-40, vol. 13, No. 1.
Treanor, John J., et al., "Evaluation of trivalent, live, cold-adapted (CAIV-T) and inactivated (TIV) influenza vaccines in prevention of virus infection and illness following challenge of adults with wild-type influenza a (H1N1), a (H3N2), and B viruses," Vaccine, Dec. 1999, pp. 899-906, vol. 18, Nos. 9-10.
Turker, Selcan, et al., "Nasal route and drug delivery systems," Pharnn. World Sci., Jun. 2004, pp. 137-142, vol. 26, No. 3.
Van Ginkel, Frederik W., et al., "Vaccines for mucosal immunity to combat emerging infectious diseases," Emerg. Infect. Dis., Mar.-Apr. 2000, pp. 123-32, vol. 6, No. 2.
Velasquez, Lissette S., et al., "An Intranasally Delivered Toll-Like Receptor 7 Agonist Elicits Robust Systemic and Mucosal Responses to Norwalk Virus-Like Particles," Clin. Vaccine Immunol., Dec. 2010, pp. 1850-1858, vol. 17, No. 12.
Wimer-Mackin, S., et al., "An intranasal vaccine targeting both the Bacillus anthracis toxin and bacterium provides protection against aerosol spore challenge in rabbits," Vaccine, May 2006, pp. 3953-3963, vol. 24, No. 18.
Yuki, Yoshikazu, et al., "Mucosal vaccines: novel advances in technology and delivery," Expert Rev. Vaccines, Aug. 2009, pp. 1083-1097, vol. 8, No. 8.
International Search Report and Written Opinion for PCT/US2010/061993 dated Dec. 23, 2010. 12 pages.
International Preliminary Report on Patentability for PCT/US2010/061993 dated Jun. 26, 2012. 7 pages.

* cited by examiner

STABILIZED VIRUS LIKE PARTICLES HAVING ENHANCED MUCOSAL IMMUNOGENICITY

FIELD OF INVENTION

This invention is directed to compositions and methods for inducing immune response. Specifically, the invention is directed to a composition comprising a subunit antigen stabilized by a polysaccharide-containing plant extract, in which the antigen consists of virus-like particles that have enhanced mucosal immunogenicity as a result of the stabilization.

BACKGROUND OF THE INVENTION noroviruses (known as Norwalk-like viruses or Norwalk viruses) are enteropathogenic viruses that cause acute gastroenteritis in adults and children. Viruses belonging to the genera norovirus are responsible for over 90% of all non-bacterial gastroenteritis epidemics [1] and a leading cause of global diarrhea [2]. The high prevalence of norovirus infections has led investigators to develop vaccine candidates to prevent disease [3]. Norwalk virus (NV) is the prototype virus of the genera norovirus and extensive preclinical studies in mice have shown that NV virus-like particles (VLPs) administered parenterally, orally, or intranasally are immunogenic [3-9]. In clinical trials, NV VLPs administered orally or intranasally have been shown to be well tolerated and modestly immunogenic [10-12]. Despite promising results, many challenges to developing a norovirus vaccine remain. A key obstacle has been the incomplete understanding of the immune correlates of protection [3, 9, 13], although a recent publication by Reeck at al. showed that antibodies that block histoblood group antigen binding to NV VLPs correlate with protection against clinical NV gastroenteritis [14].

In developing countries, according to a 2008 estimate by CDC researchers, up to 200,000 children under 5 years old die of norovirus infection each year. There is no vaccine against norovirus and no specific antiviral drugs to treat infections.

Norwalk virus is a round, nonenveloped, ~27-nm virion. Its nucleic acid contains single-stranded, positive-sense RNA. It has a single structural protein characteristic of a calicivirus. The single, positive strand of Norwalk virus RNA contains three open reading frames, the second of which is known to encode a single NV capsid protein (NVCP) that self-assembles into empty virus-like particles (VLPs) lacking viral RNA when expressed in the baculovirus/insect cell expression system. X-ray crystallography of recombinant NV VLPs (rNV VLPs) showed that these VLPs are composed of 90 dimers of the NVCP that form T=3 icosahedral structure with a diameter of about 38 nm.

The rNV VLPs are stable at low pH, when lyophilized, and when stored long term at 4° C. The insect cell-derived VLPs are immunogenic in experimental animals and in human volunteers following oral administration (Ball et al., "Oral Immunization with Recombinant Norwalk Virus-Like Particles Induces a Systemic and Mucosal Immune Response in Mice," J Virol 72: 1345-1353 (1998), Ball et al., "Recombinant Norwalk Virus-Like Particles Given Orally to Volunteers: Phase I Study," Gastroenterology 117: 40-48 (1999)), and in mice when administered parenterally (Jiang et al., "Expression, Self-Assembly, and Antigenicity of the Norwalk Virus Capsid Protein," J Virol 66: 6527-6532 (1992)), and intranasally (Guerrero et al., "Recombinant Norwalk Virus-Like Particles Administered Intranasally to Mice Induce Systemic and Mucosal (Fecal and Vaginal) Immune Responses.," J Virol 75: 9713-9722 (2001)). These qualities make the rNV VLPs useful as a candidate for vaccine against noroviruses, including Norwalk virus.

noroviruses cause greater than 90% of nonbacterial gastroenteritis outbreaks and an estimated 23 million cases of gastroenteritis in the U.S. per year. Although, the Norwalk strain of norovirus was the first discovered, it is now apparent that the Norwalk virus causes less than 10% of gastroenteritis cases, whereas other members of the norovirus family, such as the Lordsdale virus, Toronto virus, Hawaii virus and Snow Mountain virus, may cause 90% of cases.

The symptoms of norovirus infection include simultaneous diarrhea and vomiting as well as fever, headaches, chills and stomach-aches. The cause of such symptoms may be related to the binding of noroviruses to carbohydrate receptors of intestinal epithelial cells, which results in an imbalance in ion transfer.

Extremely contagious, noroviruses can cause disease by infection with as few as 10 virions. Although, otherwise healthy people infected with noroviruses may recover within 2-4 days, they may still shed virus for up to 2 weeks after the onset of symptoms; hence, infected individuals should be quarantined for up to two weeks. Approximately 30-40% of infected people may remain symptom-free, though spread infection by shedding of virus to others who may be more susceptible to infection.

Recent estimates obtained by using new and improved diagnostic assays developed over the past decade for the detection of NV infections indicate that greater than 90% of outbreaks of acute nonbacterial gastroenteritis are caused by NV or Norwalk-like agents. Outbreaks frequently occur in day care centers, schools, nursing homes, hospitals, and the military. The increasing clinical significance of these infections suggests that an effective vaccine could be useful.

Most nonreplicating proteins administered alone by mucosal routes induce poor if measurable immune responses. Therefore, there remains a need for an improved therapy for treating patients having gastroenteritis associated with norovirus or sapovirus infection and methods for preventing the spread of infection.

The most effective means to prevent infectious diseases like norovirus is through vaccination strategies that initiate immune responses at the natural site of infection, the mucosa [15]. Currently, the majority of licensed vaccines are administered parenterally; however, these vaccines have the disadvantages of patient reluctance to tolerate needle sticks and lack of mucosal immune induction [16]. Previous studies have evaluated the immunogenic potential of oral, nasal, rectal, and vaginal routes of vaccine administration [17-28]. The nasal cavity is a promising site for vaccine delivery because it is easy to access, is highly vascularized, has a relatively large surface area, has low proteolytic activity, and is able to induce systemic immunity as well as both local and distal mucosal immunity via the Common Mucosal Immune System (CMIS) [16, 29-32]. An intranasal influenza vaccine was approved for clinical use by the U.S. Food and Drug Administration (FDA) [33-35] and other intranasal vaccines for hepatitis B virus (HBV), measles, anthrax, bacterial meningitis, and others are being evaluated [18, 36]. Additional VLP-based, nasal vaccines have been shown to induce distal mucosal and systemic immunity in mice [37, 38]. The nasal route has also been shown to be superior to parenteral administration for VLP-based vaccines at eliciting IgA at distal mucosal sites [39].

Nasally administered vaccines initiate an immune response through the nasal-associated lymphoid tissue (NALT) [32, 40]. The NALT is composed of an assembly of antigen-reactive cells including B cells, T cells, and antigen presenting cells (APCs). Upon nasal vaccine administration, antigens can be taken up by specialized epithelial cells called microfold cells (M cells), or by macrophages and dendritic cells, which in turn leads to the activation of T and B cells [40, 41]. Without an adjuvant or mucoadhesive, most nasal vaccines do not elicit an immune response due to the rapid clearance of antigens [32]. The addition of mucoadhesive compounds to the vaccine formulation increases the residence time in the nasal cavity, thus increasing antigen uptake by M cells and other APCs, and enhancing the immune response [30, 32, 42].

SUMMARY OF THE INVENTION

In one embodiment, the invention provides a dry powder vaccine composition comprising virus-like particles from viruses such as norovirus capsid protein (NoVCP), human papillomavirus L1 protein, hepatitis B core protein (HBcAg), hepatitis C core protein (HCcAg) in combination with an anionic polysaccharide such as an Aloe plant extract, low-methoxy pectin, Xanthan, carboxymethylcellulose, alginate or their combination either alone or in combination with hemagglutinin (HA), neuraminidase (NA), and matrix 1 (M1) proteins; wherein the anionic polysaccharide stabilizes the virus-like particles at a pH over 6.5.

In another embodiment, the invention provides a dry powder vaccine composition comprising a virus-like particle such as norovirus capsid protein (NoVCP) of a GI, GII, GIII, or GIV genotype; and a low methoxy pectin polysaccharide derived from Aloe plant extract, wherein said Aloe extract stabilizes the virus-like particle at a pH over 6.5. It is a particular feature of the invention that in addition to stabilizing the virus-like particles, the polysaccharide acts to enhance the immune response to the composition such that the composition does not require and hence is substantially free of other adjuvants and/or TLR agonists.

In one embodiment, the invention provides a method of producing an immune response in a subject, comprising the step of intranasally administering to the subject a dry powder vaccine composition that comprises a dry powder containing a subunit antigen comprising virus-like particles, wherein said subunit antigen is stabilized by a polysaccharide-containing plant extract at a pH over 6.5.

BRIEF DESCRIPTION OF THE DRAWINGS

The invention will be better understood from a reading of the following detailed description taken in conjunction with the drawings in which like reference designators are used to designate like elements, and in which:

FIGS. 1A and 1B show: Visualization of polymer-containing powders.

FIGS. 2A-2C show: Ultrastructural characterization of polymer-containing powders by scanning electron microscopy.

FIG. 3 shows: Evaluation of VLP stability in the nasal powder by sucrose gradient sedimentation.

FIGS. 4A-4C show: Serum NV-specific IgG and IgG isotype production following intranasal immunization with VLPs in the nasal powder or PBS liquid.

FIG. 5 shows: Mucosal NV-specific IgA and IgG production following intranasal immunization with VLPs in the nasal powder or PBS liquid.

FIGS. 6A and 6B show: Vaginal NV-specific IgA and IgG production following intranasal immunization with VLPs in the nasal powder or PBS liquid. Guinea pig vaginal lavages were collected on days 0, 13, 42, and 60 and analyzed for NV VLP-specific IgA (6A) and IgG (6B) by ELISA. Background levels of vaginal antigen-specific IgA were detected in most pre-immune samples (GMT<2); antigen-specific IgG was not evaluated in pre-immune samples (data not shown). Error bars represent the standard errors of the mean. Horizontal dashed line indicates the limit of detection for the assay. ^P<0.05; *P<0.01 compared to the the nasal powder alone control group.

FIG. 7 shows: IL-8 secretion by HEK-293XL cells expressing TLR7 following stimulation with GARD in the nasal powder.

FIGS. 8A-8C show: Serum NV-specific IgG and IgG isotype production following intranasal immunization with VLPs in a polymer liquid or PBS liquid.

FIGS. 9A and 9B show: Fecal and vaginal NV-specific IgA production following intranasal immunization with VLPs in a polymer liquid or PBS liquid.

FIG. 10 shows: Mucosal NV-specific IgA production following intranasal immunization with VLPs in polymer liquid or PBS liquid.

DETAILED DESCRIPTION OF THE INVENTION

This invention relates in one embodiment to compositions and methods for inducing immune response. In another embodiment, the invention relates to a composition comprising a subunit antigen stabilized by a polysaccharide-containing plant extract, in which the antigen consists of virus-like particles that have enhanced mucosal immunogenicity as a result of the stabilization by the polysaccharide-containing extract.

The term "virus-like particle" (also referred to herein as "VLP") as used herein refers to self-assembling particles which have a similar physical appearance to virus particles and includes pseudoviruses. Virus-like particles may lack or possess dysfunctional copies of certain genes of the wild-type virus, and this may result in the virus-like-particle being incapable of some function which is characteristic of the wild-type virus, such as replication and/or cell-cell movement. Thus, typically, a virus-like particle does not carry genetic information encoding for the proteins of the virus-like particle. In general, virus-like particles lack the viral genome and, therefore, are noninfectious. In one embodiment, virus-like particles can often be produced in large quantities by heterologous expression and can be easily purified. Some virus-like particles may contain nucleic acid distinct from their genome.

A virus-like particle is typically nonreplicative and noninfectious since it lacks all or part of the viral genome, in particular the replicative and infectious components of the viral genome. A virus-like particle may also contain one or more heterologous nucleic acids distinct from the viral genome. A typical and preferred embodiment of a virus-like particle is a viral capsid such as the viral capsid of the corresponding virus, bacteriophage, or RNA-phage.

The terms "viral capsid" or "capsid", as interchangeably used herein, refer to a macromolecular assembly composed of viral protein subunits. Typically, the viral protein subunits assemble into a viral capsid, which has a structure with an inherent repetitive organization, that is typically spherical or tubular. For example, the capsids of RNA-phages or HBcAg's have a spherical form of icosahedral symmetry.

The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Non-enveloped viral particles are made up of a proteinaceous capsid that surrounds and protects the viral genome. Enveloped viruses also have a capsid structure surrounding the genetic material of the virus but, in addition, have a lipid bilayer envelope that surrounds the capsid. In a preferred embodiment of the invention, the virus-like particles are free of a lipoprotein envelope or a lipoprotein-containing envelope. In a further preferred embodiment, the virus-like particles are free of an envelope altogether.

In one embodiment, the term "antigen" refers to a molecule capable of being bound by an antibody or a T cell receptor (TCR) if presented by MHC molecules. The term "antigen" also encompasses T-cell epitopes. An antigen is additionally capable of being recognized by the immune system and/or being capable of inducing a humoral immune response and/or cellular immune response leading to the activation of B- and/or T-lymphocytes. This requires in one embodiment that, at least in certain cases, the antigen contains or is linked to a T helper cell epitope (Th cell epitope) and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

In another embodiment, the term "antibody" refers to molecules which are capable of binding an epitope or antigenic determinant. The term is meant to include whole antibodies and antigen-binding fragments thereof, including single-chain antibodies. Most preferably the antibodies are human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals.

In one embodiment, the term "epitope" refers to portions of a polypeptide having antigenic or immunogenic activity in an animal, preferably a mammal, and most preferably in a human. An "immunogenic epitope," refers to a portion of a polypeptide that elicits an antibody response or induces a T-cell response in an animal, as determined by any method known in the art. (See, for example, Geysen et al., Proc. Natl. Acad. Sci. USA 81:3998 4002 (1983)).

The term "antigenic epitope," refers to a portion of a protein to which an antibody can immunospecifically bind as determined by any method well known in the art. Immunospecific binding excludes non specific binding but does not necessarily exclude cross reactivity with other antigens. Antigenic epitopes need not necessarily be immunogenic. Antigenic epitopes can also be T-cell epitopes, in which case they can be bound immunospecifically by a T-cell receptor within the context of an MHC molecule.

The expression "protective immunity" as used herein is intended to mean the ability of an animal, such as a mammal, bird, or fish, to resist (delayed onset of symptoms or reduced severity of symptoms), as a result of its exposure to the antigen of a pathogen, disease or death that otherwise follows contact with the pathogen. Protective immunity is achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes that result in sIGA production by B lymphocytes on mucosa-lined tissues of the body. Mucosal immunity can be stimulated by an oral or intranasal vaccine. The primary result of protective immunity is the destruction of the pathogen or inhibition of its ability to replicate itself.

The expression "humoral immunity" as used herein means the result of IgG antibodies and IgM antibodies in serum.

The expression "cellular immunity" as used herein can be achieved through cytotoxic T lymphocytes or through delayed-type hypersensitivity that involves macrophages and T lymphocytes, as well as other mechanisms involving T cells without a requirement for antibodies.

The term "immunopotentiator" as used herein is intended to mean a substance that, when mixed with an antigen, enhances immunogenicity or antigenicity and provides a superior immune response. It will be recognized that it can enhance the expression of co-stimulators on macrophages and other antigen-presenting cells.

In accordance with the present invention, there is provided a virus-like particle either alone, or carrying immunogen in fusion with, endogenous viral proteins, therefore forming a new type of immunogen-carrier being also capable of immunopotentiation or having an adjuvant effect.

In one embodiment of the present invention, there is provided a class of carriers which when linked genetically to an immunogen or hapten can enhance the host's immune response to the immunogen or hapten regardless of whether the complex is administered parenterally, enterally or orally. In addition their use does not result in the formation of large lesions at injection sites.

According to the present invention, it is possible to immunopotentiate, or boost an immune reaction against a given antigen using the compositions of the present invention. The antigen may be the virus-like particles of the viruses described about but advantageously, the virus-like particles may also comprise a heterologous protein that is in immunogen. It is known particularly that small molecules often act only poorly as immunogens in their ability to elicit antibodies in an in vivo system. When attached to an immunogenic virus-like particle based compositions of this invention, that itself is antigenic, it will give rise to improved antibody response to the smaller molecule. The small molecule attached to the VLP in the present invention may be called a hapten or antigen, and can vary in size from small to quite large. In one example of this combination, of interest to the health care field, a small portion of the Hepatitis B surface antigen, comprising a sequence of determined amino acids, which is not itself antigenic, can be covalently bound to the VLP and the resulting conjugate will elicit antibodies in an in vivo system that may cross-react with the native surface antigen of the VLP and also strongly with the whole hepatitis virus.

An immunogen may be coupled to a VLP to form an immunogen-VLP complex and may then be used in a host in order to provoke an immune response. The immunogen may be specific or recognized for surface structures on T cells, B cells, NK cells and macrophages but not for Class I or Class II APC associated cell surface structures.

The immunogen to which the VLP is coupled may comprise peptides, haptens, carbohydrates, proteins, nucleic acids, and part of viruses, bacteria, parasites and other whole microorganisms. Regardless of the immunogen selected, it must be coupled to the carrier VLP in such a way as not to interfere with the recognition of the immunogen by the host's immune system as an antigenic entity.

The immunogen-VLP complex may be used as a vaccine to raise an immune response in the host. The complex initially may be given in an appropriate dosage in order to elicit an immune response. This may be followed by boosting with the complex or immunogen alone. A variation of this approach may include the formation of one or more immunogen-VLP complexes wherein one or more forms of an immunogen are coupled to one or more carrier VLPs and a plurality of such compositions is administered.

The purpose of administering the immunogen-VLP complex is to provide protection to the host in the form of immunity to the antigen and to avoid the use of adjuvants which have undesired side effects.

In one embodiment, the antigen may be as small an immunogen as a hapten or may be relatively large, such as part of a virus. The size and type of antigen is not critical to the practice of this invention. Any antigen may be used for which an immune response is desired in a host. The invention is especially useful, however, for small weakly immunogenic haptens.

Once the immunogen-VLP complex or complexes are formed, the complex or complexes may be administered to the host. The administration regime need not differ from any other generally accepted vaccination programs. A single administration in an amount sufficient to elicit an effective immune response may be used. Alternatively, other regimes of initial administration of the complex followed by boosting with antigen alone or one or more complexes may be used. Similarly, boosting with either the complex or antigen may occur at times that take place well after the initial administration if antibody titers fall below acceptable levels.

A further embodiment of the present invention is that as the VLPs have a regular multivalent and true helical structure which can be more immunogenic than aggregation of protein or free subunits of proteins, it can be easily assembled from an encoding nucleic acid. Also the greater stability of the particle can provide a long lasting exposure of the immunogen portion to the immune system. In the present invention the stability of these VLPs is further enhanced by the use of stabilizing polysaccharide compositions as described herein.

The virus portion on which the immunogen is attached, is preferably disposed on the outer surface of the VLP The host cell can be infected initially with virus or pseudovirus in particle form (i.e. in assembled rods comprising nucleic acid and a protein) or alternatively in nucleic acid form (i.e. RNA such as viral RNA; cDNA or run-off transcripts prepared from cDNA) provided that the virus nucleic acid used for initial infection can replicate and cause production of whole virus particles having the chimeric protein.

The viral portion of the chimeric protein may be any protein, polypeptide or parts thereof, derived from a viral source including any genetically modified versions thereof (such as deletions, insertions, amino acid replacements and the like) that will assemble into a VLP. A fusion protein molecule can assemble into a VLP with other fusion protein molecules or with wild-type coat protein into an immunogen-VLP virion.

Preferably, the heterologous polynucleotide coding for the heterologous protein (immunogen) portion is inserted at or adjacent a terminus of the polynucleotide coding for the viral portion, such that upon translation, the fusion protein has the viral portion at one end and the immunogen portion at the opposite end. It is not necessary for the viral portion to comprise a whole virus coat protein, simply that the viral portion forms a virus-like particle.

Preferably, the host cell used to replicate the virus or pseudovirus is a bacteria, where the virus is a plant virus, although plant cells, insect cells, mammalian cells and bacteria can be used with viruses which will replicate in such cells. The cell is preferably a bacterium such as *E. coli* although other forms of bacteria and other cells may be useful, such as cells mentioned above. The cell may be a natural host cell for the virus from which the virus-like particle is derived, but this is not necessary.

According to a particular embodiment of the present invention, the whole virus-like particle is used in combination with a stabilizing polysaccharide compositions as described herein for stable and long lasting presentation of peptide epitopes for the vaccination of animals or humans.

According to another embodiment of the present invention, the virus like particles prepared in a combination with the polysaccharides described herein appear to be very stable and can be stored easily at room temperature. Preferably, these compositions resist very high temperature and adverse conditions.

Alternatively, the VLP in combination with the polysaccharide compositions described herein can be used alone as immunopotentiator or adjuvant to enhance an immune response in humans or animals against the viruses themselves. It is preferable that the adjuvant or immunopotentiating composition comprising the VLP in combination with the polysaccharides be administered concomitantly with the antigen against which an immune response must be raised. However, the adjuvant VLP can be administered previously or subsequently to, depending on the needs, the administration of the antigen to patients, humans or animals.

In a preferred embodiment, the invention provides a composition comprising an anionic polysaccharide and a virus-like particle (VLP), such that the immune response of a host to the composition is enhanced when the composition is administered to the host as compared to the immune response that would be observed solely in the presence of the VLP, wherein the polysaccharide may comprise a low-methoxy pectin, Xanthan, carboxymethylcellulose, alginate or their combinations or any other anionic polysaccharide such as those from plant extracts described in U.S. Pat. No. 7,494,669, incorporated herein by reference. More particularly, the virus-like particles may be formed from any virus but in preferred embodiments are formed from human papillomavirus virus, hepatitis B virus, Influenza virus, and a norovirus.

Typically, vaccines are administered in the form of liquids. This administration has the significant disadvantage of poor stability and the need for refrigeration. Refrigeration creates problems in that it is prone to disruption, and is costly. Cold temperatures can also be viewed as a potential drawback to vaccines as they can cause freeze-damage rendering a vaccine obsolete, small protein molecules are particularly sensitive to freeze-thawing processes. In contrast to these traditional vaccines, a preferred vaccine formulation of the present invention is preferably a powder formulation for nasal delivery formulated such that it undergoes in situ gelling upon contact with nasal fluids. It is based on a distinct and inert ionic polysaccharide (polygalacturonic acid) that enhances the immune response through (1) prolonged nasal residence, (2) sustained antigen release by an in situ gelation mechanism, and (3) stabilization of norovirus (NoV) virus-like particle (VLP) for enhanced mucosal immunogenicity. The dry powder vaccine thus overcomes the storage and administration shortcomings of the current NoV oral vaccines. The nasal vaccine of the present invention induces both mucosal and systemic immune responses while providing protection from two dominant norovirus genotypes. The vaccine combines the NoV VLP Genotype-I and Genotype II antigens, which holds the strong potential to offer prophylactic protection. It is contemplated that the vaccine of the present invention may be prepared using antigens from other viruses or virus genotypes. Preclinical studies with this vaccine have shown robust mucosal and humoral immune responses in two test animal species, including studies demonstrating that intranasal immunization in the powder vaccine formulation of the invention provides superior mucosal immune responses to NoV antigens The invention uses VLPs created from various viruses, including e.g., the noroviruses. Currently, there are at least four norovirus genotypes (genotype I (GI), genotype II (GII), genotype III (GIII), and genotype VI (GIV)), which in turn are divided into approximately 20 genetic clusters. The caliciviruses are grouped on the basis of morphology, size, protein profile, and nucleic acid. Norwalk virus and some other human caliciviruses share considerable genetic homology.

In one embodiment, NV is classified as a human calicivirus based on sequencing and characteristics of the viral genome (positive-sense, singlestranded, nonenveloped RNA viruses with a single capsid protein). NV and NV-like agents are difficult to study because they cannot be cultivated in cell culture systems, and no animal model is available. In another embodiment, cloning and expression of the single capsid protein resulted in the assembly of empty virus-like particles that are similar to native norovirus virions in size and appearance. In another embodiment, the virus-like particles are stable at low pH, so they can be administered orally or intranasally. In another embodiment, the unique structure of the single protein that folds to make a virus-like particles indicates that these particles can be modified to be an antigen delivery system.

The genome of NV consists of a single-stranded, positive sense RNA of about 7.6 kilobases, organized into three open reading frames. These open reading frames encode a nonstructural polyprotein, the major capsid protein (VP1), and the minor basic capsid protein (VP2). Recombinant expression of the VP1 in an insect cell system, results in one aspect, in the self-assembly of empty, noninfectious virus-like particles (NV-rVLPs) that are morphologically similar to the infective virion. In one embodiment, NV VLPs have a diameter of between 27-38 nm and exhibit a T=3 icosahedral symmetry. They are composed almost entirely of 180 molecules of the VP1 capsid protein organized through self assembly into 90 dimers with a few copies (<1%) of VP2 per intact VLP. The NV VLP has a continuous protein shell with prominent protrusions at all the local and strict icosahedral 2-fold axes, leaving cup-like depressions at the icosahedral 5- and 3-fold axes. VP1 consists of two principal domains; a shell (S) and a protruding (P) domain, linked together by a flexible hinge region. The N-terminal 225 residue S domain is involved in formation of the icosahedral contacts between VP1 dimers. Residues 50-225 fold into an 8-stranded antiparallel β-sandwich arrangement, which is a commonly observed structure of other viral capsids. The C-terminal P domain is further divided into two subdomains, P1 and P2. Both subdomains are rich in β-strand structures that are involved in coordinating dimer formation, with an extensive interfacial contact area of about 2000 Å$^2$.

In one embodiment, the two different domains of VP1 unfold independently in a pH-dependent manner. In one embodiment, NV VLPs undergo structural changes at the secondary, tertiary, and quaternary levels induced by changes in pH and temperature, that are well within the pH ranges found in the gastrointestinal tract. In another embodiment, conformational stability of NV-VLPs is evident at neutral and acidic pH, with peak stability at pH 4-5. In another embodiment, significant capsid disruption is observed at alkaline pH. In one embodiment, native NV-VLPs disassemble when suspended at pH 8.5, with minimal changes in the overall secondary structure of VP1 but with significant modification of the environment of some Tyr residues, which is suggestive of changes in VP1 tertiary structure due in one embodiment to an increase in the surface charge resulting from the proximity of Tyr pka (pH=10.13). These changes are attributed in one embodiment to the S-domain, since the P-domain remains in a compact folded state. In one embodiment, very few intact NV VLPs are observed by TEM at pH 8, and those that were appeared significantly smaller than those at pH 7. In one embodiment, over pH of 6.5, there is an increase in heterogeneity of the particles, indicate the presence of oligomers of VP1. In another embodiment, the disruption of capsids by pH over 6.5 indicates an important role for pH-dependent behavior in the assembly/disassembly of virions in vivo.

In one embodiment, VP1 has a theoretical isoelectric point at pH=5.6, above which the development of charged particles will create repulsion among the various subunits. Accordingly, anionic polysaccharides having a large amount of non-binding electrons act in one embodiment to stabilize the self assembling VP1 at pH values above the isoelectric point, leading to increased mutagenicity of the intact capsid.

While preferred embodiments of the invention relate to a vaccine against noroviruses. It is contemplated that the present invention may also be used to prepare vaccines against other viruses, including but not limited to papillomavirus, hepatitis B virus, hepatitis C virus and influenza virus. Papillomaviruses are small, nonenveloped, double-stranded DNA viruses. These viruses are pathogens of epithelial surfaces and cause a variety of proliferating lesions in humans. Infection by high-risk subtypes of human papillomavirus (HPV) such as HPV type 16 (HPV16) and HPV18 is directly related to the subsequent development of cervical cancer. Papillomavirus capsids are ca. 600 Å in diameter and composed of 72 pentameric capsomeres arranged in a T=7 icosahedral lattice. Each capsomere contains five monomers of L1, a 55-kDa major capsid protein. The capsid also contains approximately 12 copies of the 74-kDa L2 minor capsid protein, possibly associated with the 12 pentavalent capsomeres. Expression of recombinant L1 or L1+L2 in a variety of expression systems results in the self-assembly of virus-like particles (VLPs) that approximate the structure of native virions. In one embodiment, the virus like particles used in the methods and compositions described herein contain human papillomavirus L1 and L2 proteins. In specific embodiments, it is contemplated that the L1 and L2 spontaneously self-assemble into virus-like particles (VLPs). In another embodiment, at pH 6.8, L1 alone is unable to assemble into virus-like particles, and free pentamers or aggregated clumps of pentamers are observed. In the presence of the stabilizing L2, HPV virus-like particles form at neutral pH, with the stabilizing anionic polysaccharides described herein "locking in" the obtained capsid structure, thereby increasing the immunogenicity of the virus-like particles thus created.

In another embodiment, the virus-like particles used in the methods and compositions described herein are prepared from a Hepatitis B core protein (HBcAg). Hepatitis B virus (HBV) is an enveloped virus with a partially double-stranded circular DNA genome of approximately 3.2 kb encoding structural and nonstructural proteins. Control and clearance of acute and chronic HBV infections are dependent in one embodiment on multispecific T-cell responses directed to several HBV-encoded antigens. HBV expresses two forms of the nucleoprotein: the 21-kDa intracellular nucleocapsid (hepatitis core antigen [HBcAg]), and 240 polypeptides spontaneously assemble into a particulate structure (HBcAg) (27 nm) in the course of virion assembly and during heterologous expression in both prokaryotic and eukaryotic systems. Dimers that align along the long vertical α-helical axis comprise the subunits of the particle. Dimer clustering of subunits produces spikes on the surface of the core shell which consist of radial bundles of four long α-helices. Many parameters affect the correct assembly of hybrid core particles. Factors such as high hydrophobicity, high β-strand index, or large volume impede in certain embodiments the proper assembly-folding of chimeric core particles. In one embodiment, stabilizing the assembled capsid using the anionic polysaccharides described herein, allows for proper encapsidation of heterologous antigens, thereby increasing the immunogenicity of vaccines using HBV rPLVs.

In another embodiment, the virus-like particles used in the methods and compositions described herein contain one or a combination of hemagglutinin (HA), neuraminidase (NA), and matrix 1 (M1) proteins from influenza virus. Influenza virions are pleomorphic, enveloped particles with a diameter of 80-120 nm. The viral genome, which consists of eight negative-sense, single-stranded RNAs, has a coding capacity for ten polypeptides. The virion contains three integral membrane proteins, hemagglutinin (HA), neuraminidase (NA) and the M2 ion channel protein. Six other viral proteins are found within the virion membrane. Four of them [nucleoprotein (NP), PB1, PB2 and PA] are associated with the viral genome to form ribonucleoprotein (RNP) complexes and the other two polypeptides, M1 and NS2 [also called NEP], interact with each other. In one embodiment, virus type-specific interactions between the RNP components and other viral proteins take place during virion assembly. In another embodiment, M1 protein induces the formation of virus-like particles which bud from cell membranes and have all the structural information needed for self-assembly, interaction with cell membranes, and accomplishment of the budding process. Accordingly, provided herein is a dry powder vaccine composition comprising influenza M1-containing virus-like particles; and an alginate, wherein said alginate stabilizes the virus-like particles at a pH over 6.5.

Accordingly, provided herein is a dry powder vaccine composition comprising virus-like particles; and an anionic polysaccharide, wherein said anionic polysaccharide stabilizes the virus-like particles at a pH over 6.5. In another embodiment, the virus-like particles used in the compositions and methods described herein, are derived from a single norovirus capsid protein (NoVCP), wherein the norovirus is selected from the group consisting of GI, GII, GIII, and GIV.

In one embodiment, the anionic polysaccharide used to stabilize virus-like partilces in the compositions and methods described herein is a polysaccharide-containing plant extract. In another embodiment, the anionic polysaccharide is a low-methoxy pectin, or Xanthan, carboxymethylcellulose, alginate or their combination in other discrete embodiments of the anionic polysaccharides used to stabilize the virus-like particles used in the compositions and methods described herein. In specific embodiments, the polysaccharide containing plant extract is an inert ionic polysaccharide polygalacturonic acid.

Pectins have an α-(1→4)-linked polygalacturonic acid (Gal A) polysaccharide polymer backbone interspersed by rhamnose residues. The Gal A residues have carboxylic acid substituent groups attached to the saccharide ring. In one embodiment, the Gal A content of pectins is about 70-75%, and the rhamnose content is <2%. The rhamnose residues are α-(1→2)-linked to Gal A residues in the backbone, and induce a T-shaped kink in the backbone chain, leading to more flexibility in the polysaccharide chains. Neutral sugar side chains are attached to the rhamnose residues in the backbone, at the O-3 or O-4 position, and the rhamnose residues tend to be clustered together on the backbone. These rhamnose contain regions comprising the side chains is referred to as a "hairy region" of the pectin, while the long stretches of repeating and unbranched Gal A residues are termed the "smooth region" of the pectin.

In another embodiment, the hydroxyl and/or carboxylic acid substituents on the saccharide rings are bound to non-sugar components such as amino acid residues. The extent of rhamnose insertions and other modifications to the chain and its monomers vary depending on the plant source of the pectin. Methylation occurs at carboxyl groups of the Gal A residues, so as to form carboxylic acid methyl esters. The degree of methylation or methyl-esterification ("DM") if a pectin is defined as the percentage of carboxyl groups (Gal A residues) esterified with methanol. Based on the DM, pectins are divided into two classes, low methoxyl ("LM") pectin with a DM of <50% and a high methoxyl ("HM") pectin with a DM of >50%. In one embodiment, the anionic polysaccharide used in the compositions and methods described herein, is LM pectin.

In one embodiment, Xanthan is used as the anionic polysaccharide used in the compositions and methods described herein.

Xanthan has a β-D-glucose backbone with every second glucose unit attached to a trisaccharide consisting of mannose, glucuronic acid, and mannose. The mannose closest to the backbone has an acetic acid ester on carbon 6, and the mannose at the end of the trisaccharide is linked through carbons 6 and 4 to the second carbon of pyruvic acid.

In one embodiment, carboxymethylecellulose (CMC) is used as the anionic polysaccharide used in the compositions and methods described herein.

CMC is a cellulose derivative with carboxymethyl groups (—CH$_2$—COOH) bound to some of the hydroxyl groups of the glucopyranose monomers that make up the cellulose backbone. It is often used as its sodium salt, sodium carboxymethyl cellulose.

In one embodiment, the plant extract comprising the anionic polysaccharide used to stabilize the virus-like particles in the compositions and methods described herein, is an Aloe plant extract. Plant extracts of Aloe, containing anionic polysaccharides are described in U.S. Pat. No. 7,494,669 incorporated herein by reference in its entirety.

An exemplary powder formulation of the invention is based on a nasal powder formulation that consists of polymer, lactose, Povidone, buffer, and salts. An advantageous ingredient is the polymer (herein referred to as the polymer liquid) that gives the formulation its unique in-situ gelling property for controlling the antigen release and increasing the nasal residence time.

The polymer liquid is a chemically and functionally distinct high molecular weight anionic polysaccharide (sodium polygalacturonate, CAS RN 119758-46-2) with mucoadhesive properties extracted from Aloe vera L. The polymer liquid is characterized by a high galacturonic acid (Gal UA) content of >90%, a low degree of methylation of <10%, and a high molecular weight of >400 kDa (weight average). Due to its distinct chemical and gelling properties, the polymer is used at a very low content, 0.1-1% (w/w) of the powder. The lactose is the dominant component of the formulation, accounting for more than 90% (w/w) of the mass. The pH of the formulation is approx. ~7.0. The polymer liquid is uniquely capable of in-situ gelation, turning into a gel whether in liquid or powder form, upon contact with body fluids at the site of administration[43]. This in-situ gelation property thereby extends the mucosal residence time. Furthermore, the polymer liquid belongs to the plant polysaccharides that are "generally regarded as safe" (GRAS) by the FDA. The collection of these properties makes the polymer liquid ideal for use in intranasally administered vaccines [44].

The term "powder" refers to a solid, dry material that primarily comprises very small solid particles or spheres (as shown in FIG. 1). The largest dimension of the bulk of the particles or spheres of a powder are less than a millimeter. Preferably, the dry powder composition is milled into a composition that has particle diameters of 0.10-500 μm scale. In the context of the above definition, "dry" indicates that there is very little, if any unbound liquid (including water) on the surface of the powder particles or spheres that would tend to significantly inhibit the normally free-flowing physical characteristics of a powder. In another embodiment, the powders compositions described herein may in fact comprise absorbed water within polymer networks, but do not comprise significant amounts of unbound liquid water on their surfaces.

Those skilled in the art will readily be able to prepare the nasal powder formulation using different convention powder preparation processes. For example, formulation is first prepared as an aqueous liquid and then dried to produce the powder using either freeze drying or spray drying is were stored at ambient room temperature prior to use. The process conditions are optimized to minimize or eliminate any possible loss of the antigen or other active ingredients.

In an exemplary embodiment, the powder vaccine is prepared using a freeze drying technique. The liquid formulation is placed into vials, and freeze-dried using a vacuum dryer after freezing the formulation first in a −80° C. freezer or in a LyoStar II lyophilizer (FTS system, New York). The dried material is milled using a ball mill (Retsch MM301) followed by sieving using 40 and 100 μm sterile nylon membranes under vacuum to produce powders of <40 μm, 40-100 μm, and >100 μm. Powders of the <40 μm and 40-100 μm size are used in animal studies.

In another exemplary embodiment, the powder is prepared using spray drying techniques. This is a one-step process for making powders from a liquid formulation. A Buchi 290 spray dryer (Buchi Labortechnik AG, Flawil, Switzerland) was used to dry the same liquid formulation into powders. Spray drying conditions including the inlet temperature and spray nozzles are adjusted to produce powders with a minimal antigen loss and a mean particle size of ~20 μm with a low percentage of powder below 10 μm. Generally, 30-50 ml of liquid formulation was spray-dried. A ~60% powder yield is obtained.

Figure 2A:
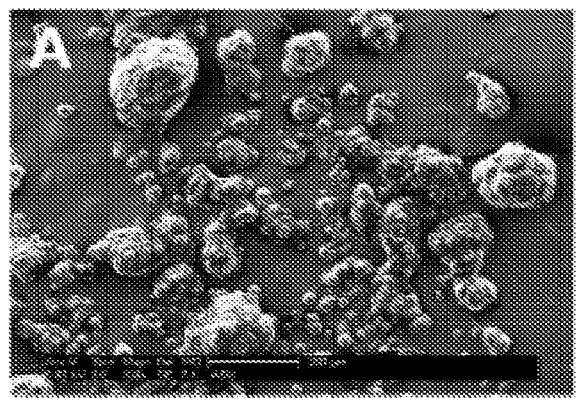
Figure 2B:
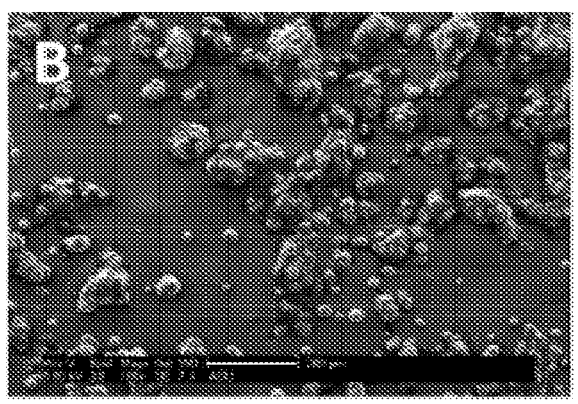
Figure 2C:
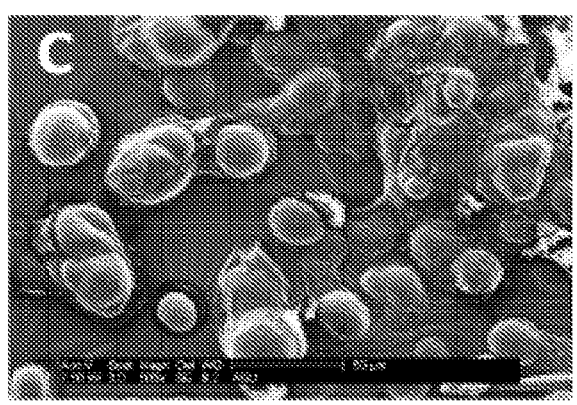

The powder formulation of this invention has been analyzed by electron microscopy. Referring now to FIG. 2, there shown is an ultrastructural characterization of polymer-containing powders by scanning electron microscopy. The polymer-containing powder alone (2A) or formulated with NV VLPs (2B, 2C). The polymer-containing particles were imaged at 100× (2A, 2B; scale bar 200 μm) and 500× (2C; scale bar 50 μm) with a scanning electron microscope. Non-aggregated particles range in size from 15-30 μm in diameter, and are smooth in appearance.

Powders containing the polysaccharide-containing plant extract, formulated with lactose, Povidone, buffer and salts but without antigen showed particulate structures in scanning electron microscopy (2A). When formulated with norovirus VLPs (2B, 2C), the structures were indistinguishable from the powders without antigen. In these studies, the polymer-containing particles were imaged at 100× (A, B; scale bar 200 μm) and 500× (2C; scale bar 50 μm) with a scanning electron microscope. Aggregation of particles occurs during sample preparation for microscopy, likely due to hydration. Non-aggregated particles range in size from 15-30 μm in diameter, and are smooth in appearance. Virus-like particles can, therefore, be included in the dry powder production process without changing the structural characterization of the powder particles.

Figure 1B:
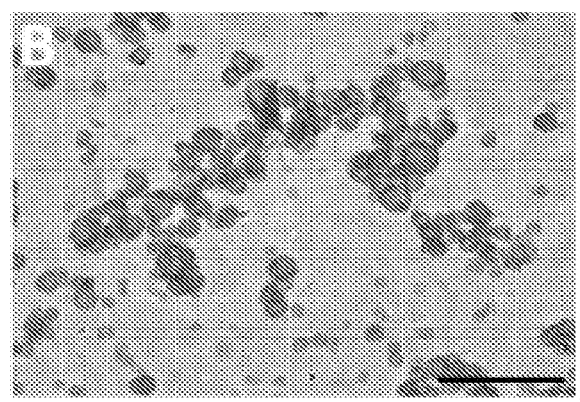

The powder formulations were also analyzed by light microscopy, before and after hydration. Referring now to FIG. 1A and FIG. 1B there shown is visualization of the polymer-containing powders. FIG. 1A shows spray dried the polymer-containing powder containing spherical-shaped particles ranging in size from approximately 20-30 μm in diameter. Aggregation of particles occurs during sample preparation for microscopy, likely due to hydration. FIG. 1B shows the polymer-containing particles reconstituted and hydrated with simulated nasal fluid and stained with toluidine blue dye. Aggregation of particles, coincident with hydration, is evident. Scale bars are 100 μm.

Spray dried polymer-containing powder contains spherical-shaped particles ranging in size from approximately 20-30 μm in diameter (A). Some aggregation of particles occurs during sample preparation for microscopy, likely due to hydration. When the polymer-containing particles were reconstituted with simulated nasal fluid and stained with toluidine blue dye, much more extensive aggregation of particles, coincident with hydration, is evident (B). Scale bars are 100 μm.

EXAMPLES

Example 1

Dry Powder Formulation of VLPs Enhances Immunogenicity

Referring again to FIG. 1A and FIG. 1B, the dry powder formulation of virus-like particles, or its equivalent rehydrated formulation, gels in situ upon contact with body fluids as a result of interacting with low levels of calcium ions in interstitial fluids or mucosal secretions. When used directly for nasal immunization, the powder formulation of virus-like particles enhances the immune response through prolonged nasal residence and sustained antigen release by the in situ gelation mechanism, resulting in both systemic and mucosal immunity. This would be analogous to the aggregation of particles observed by microscopy after hydration with simulated nasal fluid. Alternatively, the particles can be rehydrated after storage, and the resulting liquid formulation changes from a liquid to a gel in the tissues after needle delivery immunization. This occurs since the formulation still possesses in-situ gelling property and thus can be valuable for immunization by subcutaneous (SQ) and intramuscular (IM) injection; in this case it provides a strong immunoenhancing effect because it provides sustained antigen release in the tissue where the rehydrated powder was delivered by needle.

In one embodiment, the dry powder formulations were prepared by spray drying and resulted in a white, fine powder that appeared as spherical-shaped particulates as shown in FIG. 1A. The mean particle size was 20 μm as measured by a laser diffraction particle size analyzer. When rehydrated in simulated nasal fluid and stained with toluidine blue dye, particulates formed wet gel particles that were enlarged in size as shown in FIG. 1B. In vivo, this characteristic is important as mucoadhesive polymers act by swelling upon contact with the mucosa, then penetrating into the tissue crevices to increase the residence time of the antigen in the nasal cavity [30]. The dry powder formulations were prepared, processed and analyzed by scanning electron microscopy for ultrastructural characterization. The dry powders all had a similar dispersed, particulate profile with individual spherical particles ranging in size from 20-30 μm in diameter (See FIG. 2). Some aggregation was evident in the micrographs and is likely due to hydration during the sample preparation. The particle surface was non-porous in appearance (as shown in FIG. 2), consistent with other reports of spray dried subunit antigen formulations [48]. A Phase I scintigraphy clinical trial with the nasal powder and found no lung deposition in healthy human volunteers; this was related to particle size of the powder (personal communication, Jim Talton). When we compared the nasal powders with or without norovirus antigen included in the formulation, no detectable size or other structural differences were observed.

Figure 3:
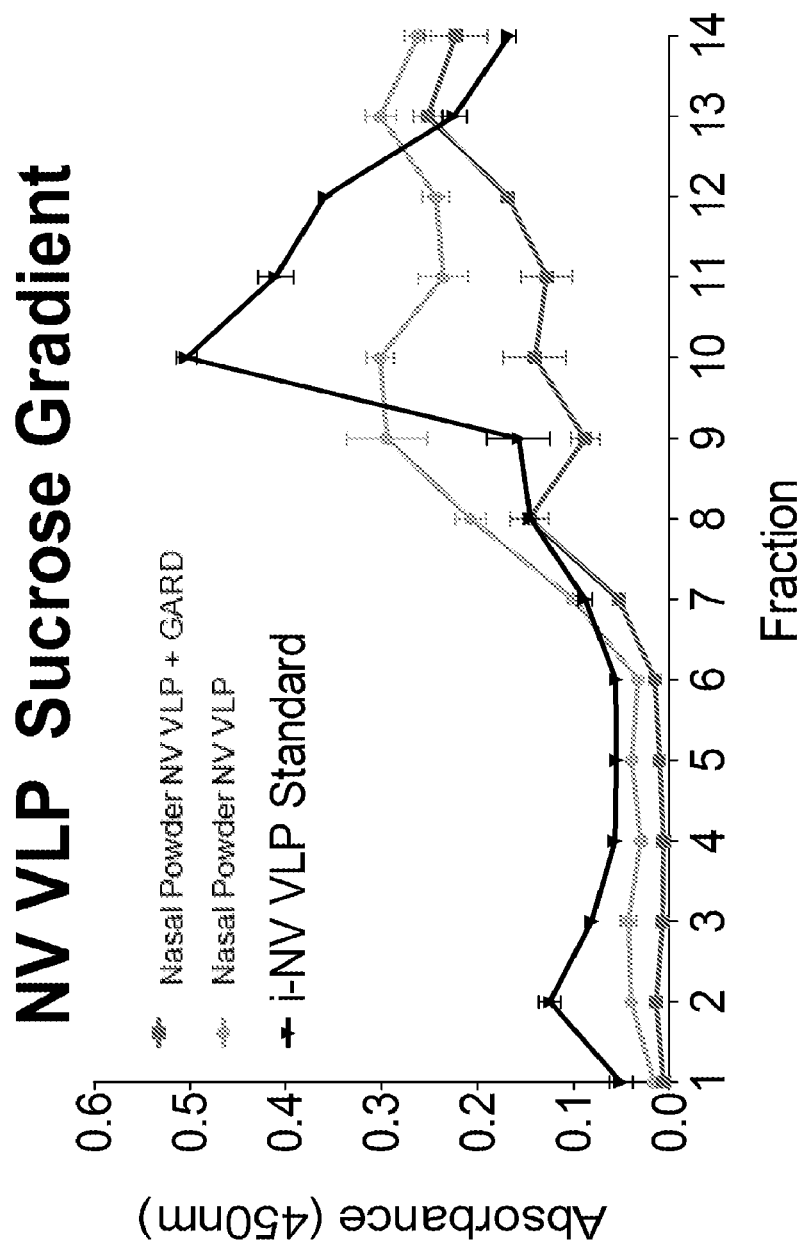

Referring now to FIG. 3, there shown is an evaluation of VLP stability in the nasal powder by sucrose gradient sedimentation. The dry powder NV VLP and NV VLP+ GARD vaccine stocks and liquid insect-cell derived NV VLP standard (i-NV VLP) were loaded onto a 6 layer sucrose density gradient and centrifuged. Fractions were removed from the gradient from top (1) to bottom (14) and analyzed by indirect ELISA for NV VLP. Peaks in the absorbance between fractions 8 and 14 correspond to whole NV VLP, indicating that NV VLP is stable in the dry powder formulation.

The spray drying process used to transform the vaccine from a liquid state to a dry powder utilizes a hot drying medium that may denature vaccine components [32]. Therefore, prior to immunization, the nasal dry powder formulations (1 mg) containing NV VLPs alone or NV VLPs and GARD were evaluated by sucrose gradient sedimentation and indirect ELISA to determine if the spray drying process influenced NV VLP stability. Particulate antigens, such as assembled VLPs, migrate more rapidly into more dense sucrose solutions as compared to unassociated or partially associated capsid protein antigens [45]. As expected, insect cell-derived NV VLPs showed most antigen content in assembled VLP fractions (fractions 8-14). The nasal dry powder formulations of NV VLPs with or without GARD also showed the majority of antigen present in fractions 8-14, indicating maintenance of VLP structural integrity throughout the formulation process, and persisting in the dry powder. A similar spray drying process used to encapsulate bovine serum albumin (BSA) into microspheres was shown to preserve antigen stability [49] and induce strong systemic immune responses when intranasally delivered to mice, suggesting that the spray dry vaccine preparation method is an effective strategy.

The spray drying process can be used to produce bulk nasal powder NoV vaccines of the invention by mixing the NoV VLPs at different dosage levels with the the Nasal™ powder. The two components are mixed in USP water for irrigation and the mixture is spray dried as described above. The spray dried vaccine formulation is then freeze dried to remove excess moisture. The bulk powder vaccine is then filled into a suitable nasal delover device such as a Monopowder MK IV powder delivery device (Pfeiffer/Valois) for nasal administration. The Monopowder MK IV is a positive pressure device and thus may be suited for infants and the young who can not inhale upon request if a passive device is used.

In one embodiment between about 25 and 250 µg of the virus-like particle are incorporated into the vaccines using the compositions described herein. In another embodiment, "Vaccine" comprises one or more antigens, in the form of a protein, a carbohydrate, a lipid, or nucleic acid, a cell in whole or part, a virus, a virus capsid, etc., that is capable of inducing immune response in a treated organism, against the antigen or the microorganism or tissue from which it is derived, so as to treat or prevent diseases caused by microorganisms, viruses, and/or or cancer.

In another embodiment, the compositions described herein are used in the methods of producing a robust immune response in a subject. In one embodiment, the term "immune response" refers to a humoral immune response and/or cellular immune response leading to the activation or proliferation of B- and/or T-lymphocytes. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant.

In one embodiment, the compositions used in the methods described herein, are formulated for intranasal administration, referring in context, to the delivery of the compositions described herein through the nasal mucosa. In another embodiment, the term "intranasal administration" of a composition and grammatical forms thereof mean delivery of the composition to any portion of the nasal epithelium.

Formulations which are useful for intranasal administration of the pharmaceutical composition of the invention include, but are not limited to powder, microsomes, liposome, sustained release, degradable polymer, polymer microspheres, impregnated microneedles, fiber, or patch, coated film, fiber, or patch, and other similar solid dosage forms.

Such pharmaceutical compositions may also contain ingredients to enhance sensory acceptability of the composition to a human patient, such as aromatic, aromatherapeutic, or pleasant-tasting substances. The pharmaceutical compositions may also, for example, be made in the form of a flexible solid or semisolid carrier comprising the compositions described herein; or in the form of suspended microspheres. In certain embodiments, the term "administered" includes but is not limited to delivery by a mucosal route, for example, as a nasal spray or aerosol for inhalation.

In one embodiment, the term "about" refers to a value that is within twenty percent, or 10% in another embodiment, or 5% in another embodiment, of the indicated value.

The term "subject" refers in one embodiment to an animal. Preferably, the subject is a mammal, including for example livestock and humans. In some aspects of the present invention, the subject may suitably be a human.

Example 2

Powder Formulation of VLPs Provides Superior Nasal Immunogenicity

Once it was determined that the spray drying process maintained NV VLP structural integrity (FIG. 3) and that the powders were appropriately rehydrated with simulated nasal fluid (FIG. 1B), the immunogenicity of the the nasal dry powder vaccines were evaluated in a guinea pig model. In comparison to conventional murine models, guinea pigs are preferred for delivery and evaluation of dry powder formulations because they provide a larger nasal mucosal surface area for immune induction. In addition, guinea pigs have been used previously to evaluate TLR7 agonist activity in vivo [50, 51]. The immunogenicity of the nasal powder vaccines were evaluated relative to complementary PBS liquid formulations of NV VLPs (10 or 25 µg) with or without GARD (10 µg). To measure systemic immune induction, serum was assayed for NV VLP-specific IgG, IgG1, and IgG2a levels by ELISA.

Figure 4A:
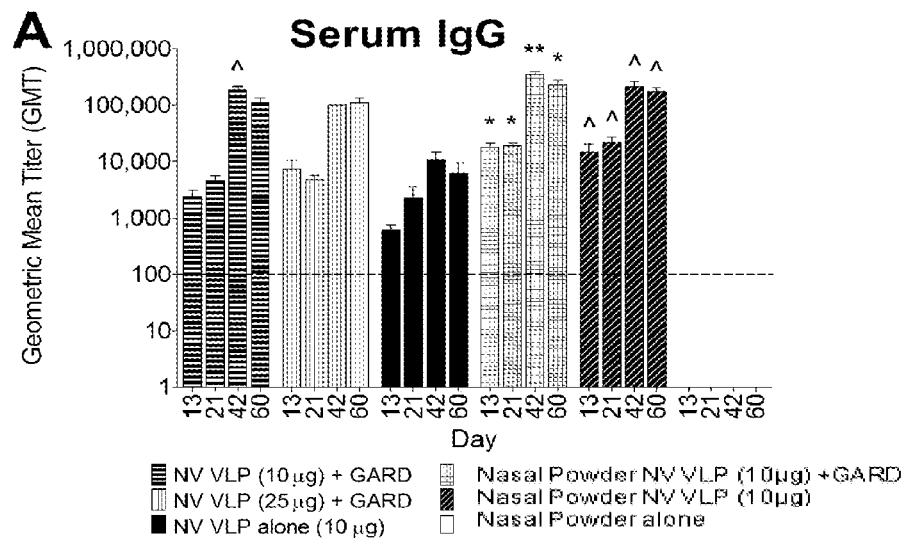
Figure 4B:
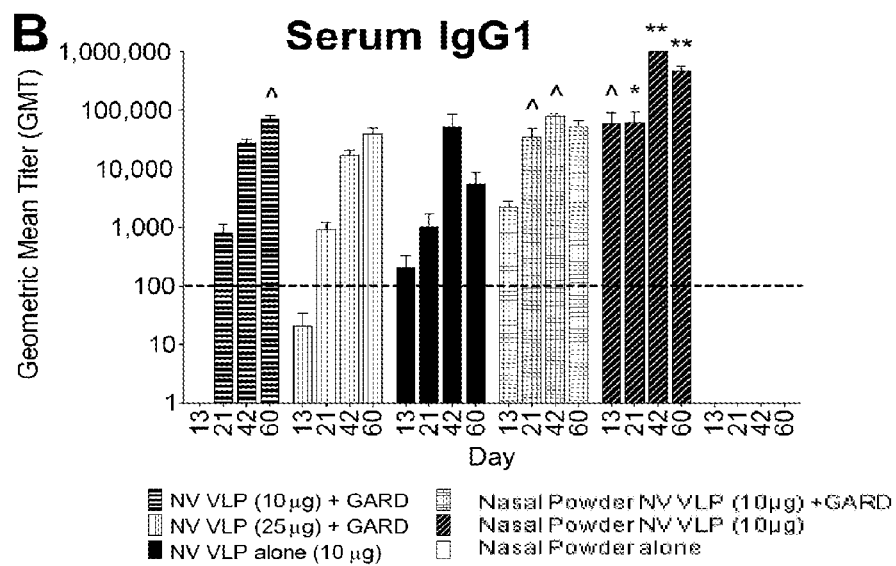
Figure 4C:
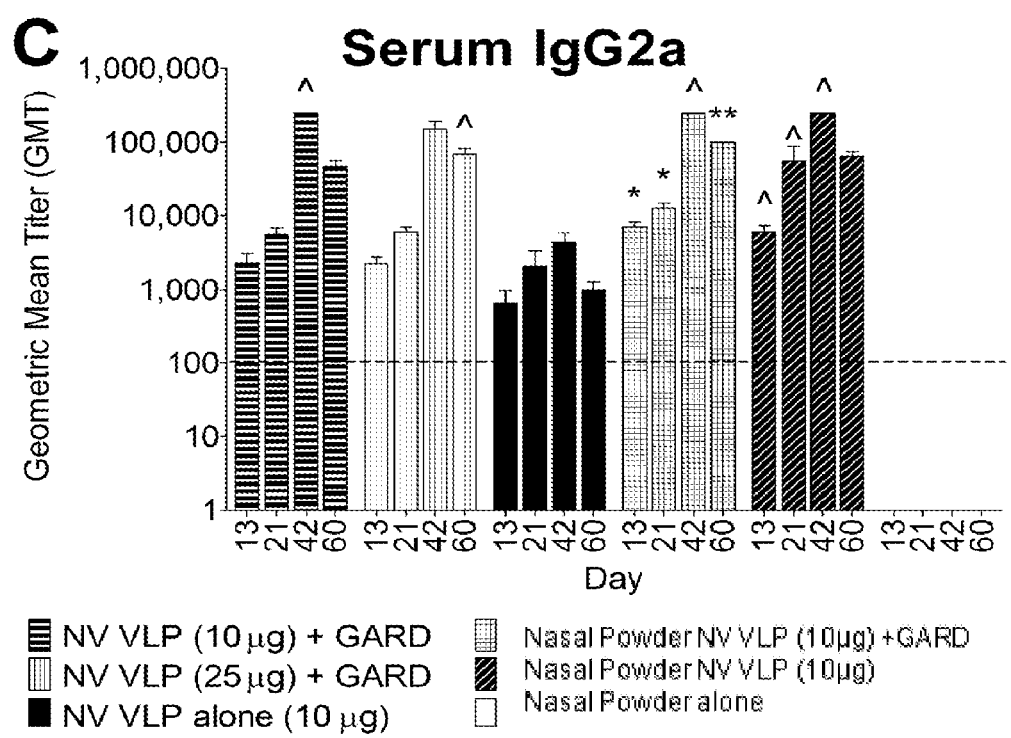

Immunization with NV VLPs, whether in a nasal powder or PBS liquid formulation, induced higher antigen-specific IgG1 production than IgG2a, indicative of a predominant Th2 response. This result is consistent with previous studies and suggests that the Th2 shift is due to the NV VLP antigen (FIG. 4B, 4C) [4, 7]. As hypothesized, the nasal powder formulations were more immunogenic than their liquid counterparts (FIG. 4). In comparison to guinea pigs immunized with the nasal powder alone powder (mock-immunized), guinea pigs immunized with NV VLP powder with or without GARD produced significantly higher antigen-specific IgG, IgG1, and IgG2a antibody titers on most days throughout the study (days 13-60) ($P<0.05$); whereas guinea pigs immunized with comparable liquid formulations rarely induced significant titers (FIG. 4). On average, the magnitude of enhancement by immunization with NV VLP powder formulated without GARD, relative to NV VLP liquid was 20-, 114-, and 40-fold for IgG, IgG1, and IgG2a, respectively (FIG. 4). These levels were statistically different on days 13, 42, and 60 for IgG1 ($P<0.05$) (FIG. 4B). The magnitude of immune response enhancement achieved by including GARD in the dry powder formulation, relative to both liquid counterparts was 4-, 300- and 2-fold for IgG, IgG1, and IgG2a, respectively (P≥0.05) (FIG. 4). Unexpectedly, GARD did not significantly enhance serum IgG and IgG isotype production (P≥0.05) when included in the dry powder formulation. The level of IgG and IgG2a production enhancement achieved by the powder vaccine without the TLR7 agonist was higher than that achieved with GARD (FIG. 4).

Figure 5:
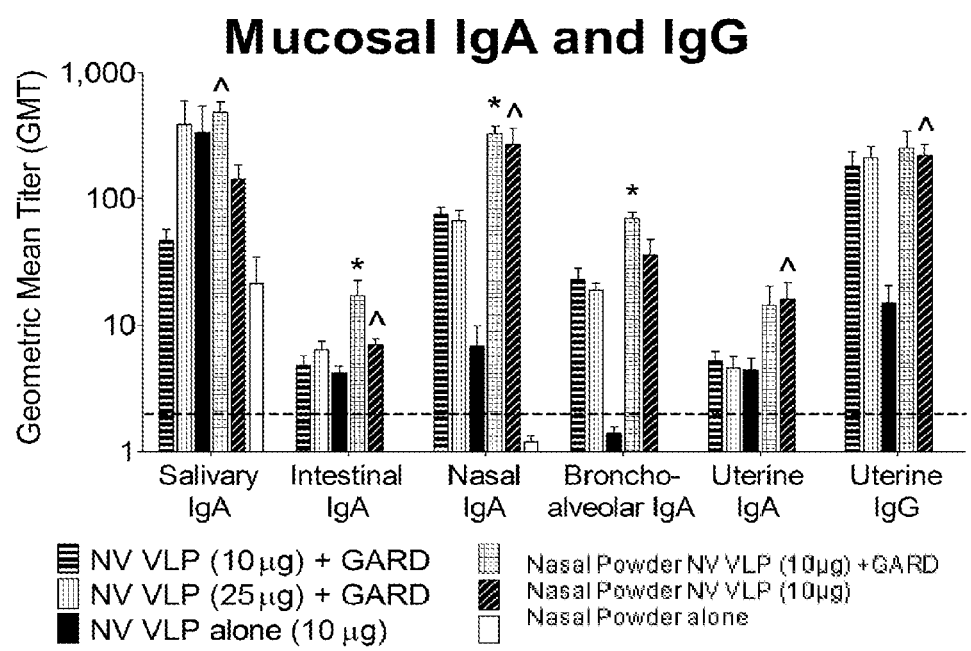

Referring now to FIG. 5, there shown ion mucosal NV-specific IgA and IgG production following intranasal immunization with VLPs in nasal powder or PBS liquid. Guinea pigs were euthanized on day 60. Salivary, intestinal, nasal, bronchoalveolar, and uterine lavages were collected and analyzed for NV VLP-specific IgA and IgG by ELISA. Error bars represent the standard errors of the mean. Horizontal dashed line indicates the limit of detection for the assay. ^P<0.05; *P<0.01 compared to the nasal powder alone control group.

Nasal powder vaccines were administered intranasally, therefore we evaluated their ability to induce strong NV-specific IgA production at the primary site of immunization, the respiratory tract. Significant IgA titers were observed in nasal and bronchoalveolar lavages collected from guinea pigs immunized with the powder formulations (P<0.05); whereas no such response was observed for the liquid formulations (P≥0.05). The NV VLP powder without GARD elicited 40- and 26-fold higher nasal and bronchoalveolar IgA production, respectively, relative to its liquid counterpart. Similarly, the NV VLP and GARD powder elicited 4- and 3-fold higher nasal and bronchoalveolar IgA production relative to both liquid counterparts (P<0.05). Interestingly, nasal and bronchoalveolar IgA titers were comparable in guinea pigs immunized with NV VLP powder or NV VLP and GARD powder, a result similar to that observed for serum IgG and IgG2a (as shown in FIG. 4A, 4C).

Gastrointestinal Tract (Salivary, Intestinal).

Still referring to FIG. 5, To gain further information related to the mucosal immunogenicity of dry powder formulations, and their ability to stimulate responses at distal sites in the CMIS, we evaluated antibody titers at multiple mucosal surfaces. Because NV initiates disease via the enteric route, IgA titers were evaluated in the enteric pathway. NV-specific IgA production was found in both saliva and intestinal lavages, with higher concentrations per volume recovered in the saliva (however higher levels of non-specific background IgA were detected in salivary samples). Powder formulations and their liquid counterparts elicited nearly equivalent IgA production in the saliva, although the NV VLP and GARD powder was the only vaccine regimen to induce statistically significant NV VLP-specific IgA production relative to mock-immunized guinea pigs (P<0.05). In the intestine, both powder formulations induced IgA responses that were higher than their liquid counterparts and significantly higher than mock-immunized guinea pigs (P<0.05). In contrast to serum IgG and IgG isotype results (as shown in FIG. 4), the addition of GARD to the powder-formulated VLPs increased salivary and intestinal IgA production by 3- and 2-fold, respectively. These levels however, were not statistically different in the sample size of this experiment (P≥0.05) (as shown in FIG. 6).

To gain insights into the extent of CMIS stimulation by Nasal powder-formulated VLPs, we evaluated NV-specific IgA and IgG production in the female reproductive tract. Vaginal and uterine IgG production was higher than IgA production (FIGS. 5, 6). As was seen in serum (FIG. 4) and the respiratory tract (FIG. 5), the NV VLP powder without GARD induced higher vaginal IgA (day 42; 11-fold) and IgG (days 13 and 21; 11-fold) as well as uterine IgA (4-fold) and IgG (15-fold) production relative to its liquid counterpart (FIGS. 5, 6). Similarly, the NV VLP and GARD powder induced higher IgA production in the vagina (days 42 and 60; 2-fold) and uterus (3-fold) relative to both liquid counterparts (FIGS. 5, 6). The addition of GARD to the powder-formulated VLPs did not consistently enhance vaginal or uterine IgA and IgG production as compared to the NV VLP powder (FIGS. 5, 6).

Figure 6A:
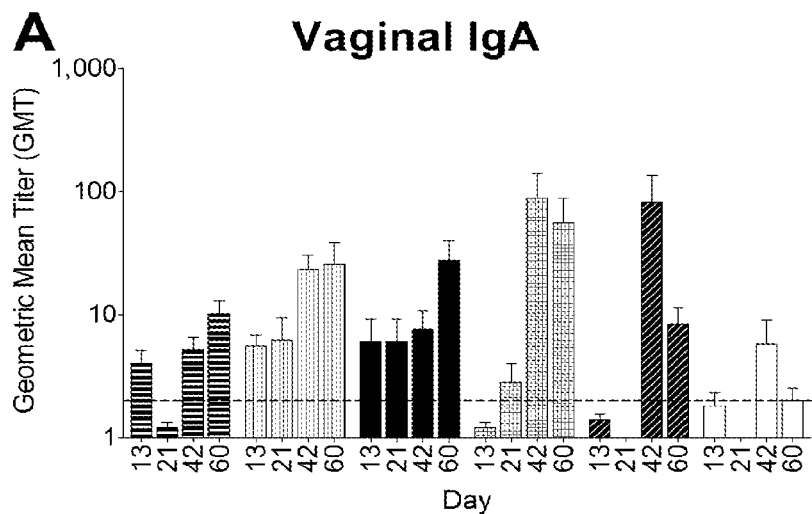
Figure 6B:
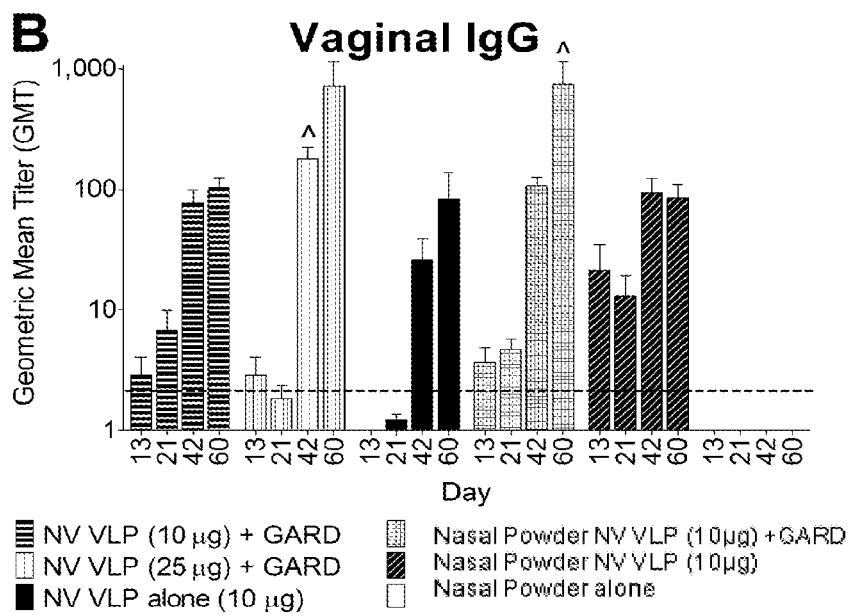

Collectively, these results indicate that our intranasal NV dry powder vaccine containing a mucoadhesive polymer liquid elicits robust systemic and mucosal immune responses that in most cases are superior to those induced by liquid counterparts without the polymer liquid (FIGS. 4, 5, 6). Prolonged nasal residence time most likely increased antigen uptake and contributed to the enhanced immune induction elicited by the Nasal powder formulations. These results are consistent with previous preclinical studies that evaluated the efficacy of intranasally delivered influenza, anthrax, and tetanus dry powder vaccines [27, 52, 53]. Like our NV vaccine, the influenza and anthrax vaccines contained a mucoadhesive polymer (chitosan); whereas, the tetanus vaccine did not contain a mucoadhesive. Despite this difference, all three dry powder vaccines induced robust systemic immune responses that were superior to those induced by comparable liquid counterparts [27, 52, 53]. In addition, similar to our NV dry powder vaccine, the tetanus and influenza dry powder vaccines elicited robust nasal IgA production at levels higher than that elicited by comparable liquid counterparts [27, 53].

Example 3

Figure 8A:
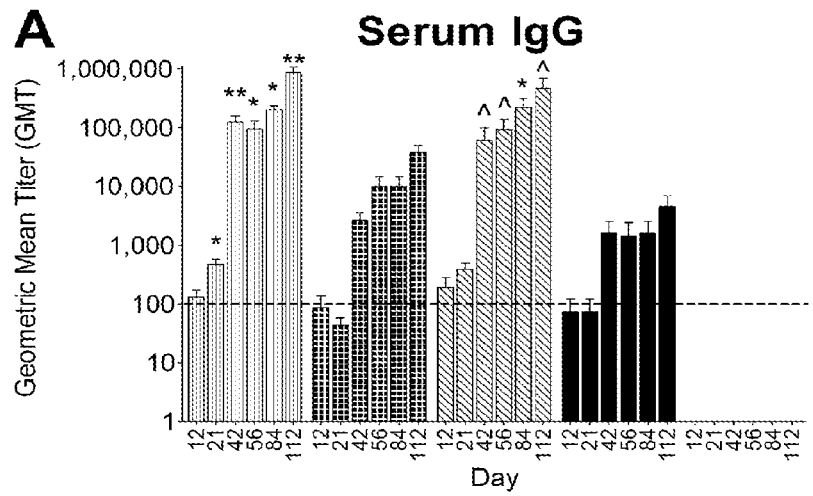
Figure 8B:
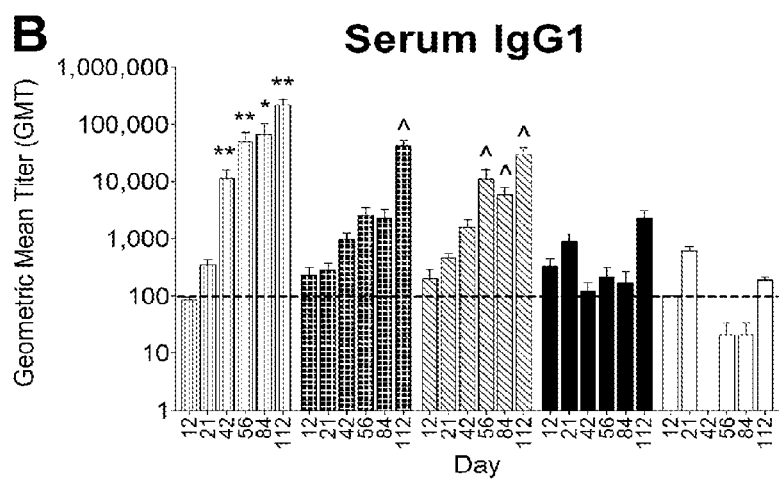
Figure 8C:
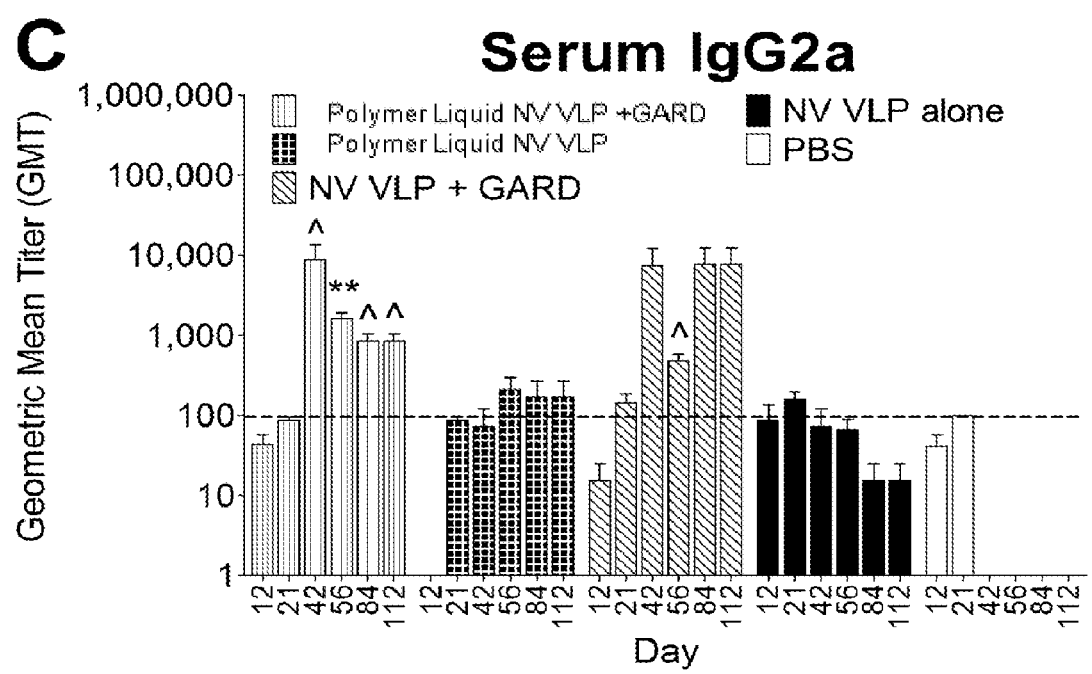

Delivery of Liquid Polymer with rVLP Antigen is not Superior to Delivery of rVLP with a TLR Agonist Referring now to FIG. 8, there illustrated are results of serum NV-specific IgG and IgG isotype production following intranasal immunization with VLPs in a the polymer liquid or PBS liquid. Female BALB/c mice were immunized intranasally with a polymer liquid or PBS liquid formulation of NV VLPs (10 µg) on days 0 and 21 with or without GARD (10 µg). Serum samples were collected on days 0, 12, 21, 42, 56, 84, and 112 and analyzed for NV VLP-specific IgG (A), IgG1 (B), and IgG2a (C) by ELISA. Antigen-specific IgG was not detected (GMT<100) in all pre-immune samples; however background levels of antigen-specific IgG1 and IgG2a were detected (GMT≥100) in most pre-immune samples (data not shown). Error bars represent the standard errors of the mean. Horizontal dashed line indicates the limit of detection for the assay. ^P<0.05; *P<0.01 compared to the PBS control group.

Conclusions from this example are that Guardiquimod is a TLR agonist that has adjuvant effects if co-delivered with rVLP in nasal immunization. When the rVLP was nasally delivered with polymer liquid aloe extract as a liquid, the immune responses were strong, but not as high as with GARD+rVLP. When GARD was included with rVLP plus polymer liquid aloe extract, the highest level of immune response was observed.

Since NV VLPs in the powder vaccine containing the polymer liquid elicited robust systemic and mucosal immune responses without an adjuvant (FIGS. 4, 5, 6), we aimed to determine if the immune responses were elicited by the dry powder formulation or potential immunostimulatory properties of the polymer liquid. Female BALB/c mice were intranasally immunized with NV VLPs alone (25 μg) or NV VLPs (25 μg) and GARD (10 μg) in PBS liquid formulations with or without the polymer liquid.

Similar to guinea pig serum results (FIG. 4), NV VLPs, whether in a polymer liquid or PBS liquid formulation, induced higher levels of serum IgG1 production than IgG2a, indicative of a strong Th2 response. When administered in a powder vaccine containing the polymer liquid, NV VLPs consistently enhanced humoral immune responses relative to liquid counterparts without the polymer liquid (FIG. 4). In contrast, when administered in a liquid vaccine containing the polymer liquid, NV VLPs did not consistently or significantly enhance serum IgG and IgG isotype production relative liquid counterparts without the polymer liquid (FIG. 8). Moreover, the addition of GARD to NV VLPs in the Nasal powder vaccine did not enhance humoral immune responses (FIG. 4); whereas, the addition of GARD to the NV VLPs in the polymer liquid liquid vaccine enhanced serum IgG (days 21-112; 22-fold), IgG1 (days 42-112; 16-fold), and IgG2a (day 12 and 42-112; 36-fold) production relative to the polymer liquid NV VLP alone formulation (FIG. 8). These levels reached statistical significance for IgG2a on day 42 ($P<0.01$) (FIG. 8).

Example 4

Delivery of Dry Nasal Powder with rVLP Antigen is a Superior Means of Nasal Immunization Referring now particularly to FIG. 4, there shown are results of a serum NV-specific IgG and IgG isotype production following intranasal immunization with VLPs in Nasal powder or PBS liquid. Female Hartley guinea pigs were immunized intranasally with a dry powder or a PBS liquid formulation of NV VLPs (10 or 25 μg) on days 0 and 21 with or without GARD (10 μg). Serum samples were collected on days 0, 13, 42, and 60 and analyzed for NV VLP-specific IgG (A), IgG1 (B), and IgG2a (C) by ELISA. Antigen-specific IgG, IgG1, and IgG2a were not detected (GMT<100) in all pre-immune samples (data not shown). Error bars represent the standard errors of the mean. Horizontal dashed line indicates the limit of detection for the assay. ^$P<0.05$; *$P<0.01$; $P<0.001$; *$P<0.0001$ compared to the Nasal powder alone control group.

Example 5

Rationale for Why the Nasal Dry Powder with rVLP Antigen is a Superior Means of Nasal Immunization Due to the distinct difference in the immunogenicity of rVLP formulations, an evaluation was made to analyze whether the determining factor could be the antigen stability or structure. There have been many prior studies showing that NoV capsid protein produced in either plant cells or insect cells will self assemble into rVLP. As discussed in Santi et al. 2008 and elsewhere, the self assembly appears to be reversible and the degree of assembly into "intact" VLPs of size similar to the virus itself can be assessed by subjecting samples to sucrose gradient separation. In the sucrose gradients, partially assembled antigen sediments slowly, whereas assembled VLPs or VLP aggregates penetrate deeply into the gradient.

Referring now particularly to FIG. 3, there shown is an evaluation of VLP stability in Nasal powder by sucrose gradient sedimentation. The dry nasal powder NV VLP and nasal powder NV VLP+GARD vaccine stocks and liquid insect-cell derived NV VLP standard (i-NV VLP) were loaded onto a 6 layer sucrose density gradient and centrifuged. Fractions were removed from the gradient from top (1) to bottom (14) and analyzed by indirect ELISA for NV VLP. Peaks in the absorbance between fractions 8 and 14 correspond to whole NV VLP, indicating that NV VLP is stable in the dry powder formulation.

Figure 7:
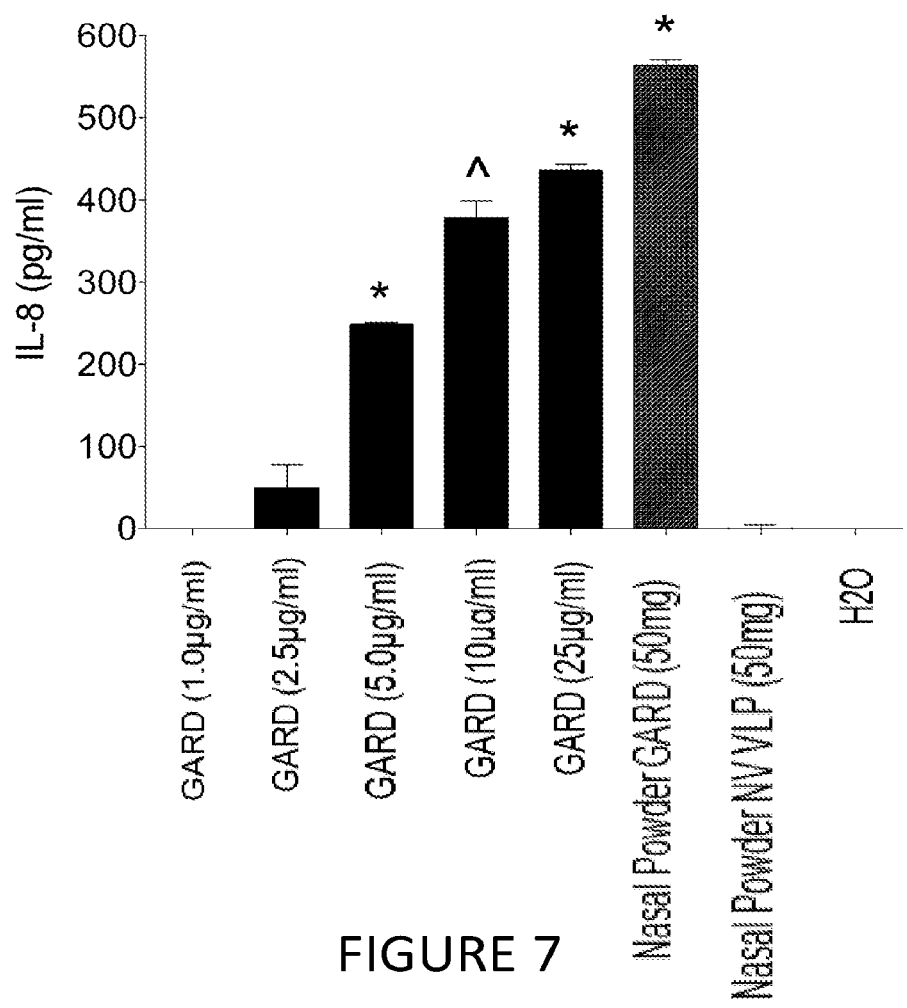

The enhanced stability of VLPs coupled with a slow in situ release of VLPs is responsible for enhanced immunogenicity of the dry powder formulation. Referring now to FIG. 7, there shown is IL-8 secretion by HEK-293XL cells expressing TLR7 following stimulation with GARD in Nasal powder. HEK-293XL cells expressing human TLR7 were cultured in 24-well plates and stimulated with 15.6 mg/ml Nasal GARD powder formulation or 1.0, 2.5, 5.0, 10, or 25 μg/ml of GARD in a PBS liquid formulation. Nasal powder NV VLP and H2O were used as negative controls. Cell culture supernatants were collected 24 h after stimulation and analyzed in duplicate for IL-8 content by ELISA. Nasal powder results are expressed as the amount of IL-8 per 50 mg of powder. Error bars represent the standard errors of the mean. ^$P<0.05$; *$P<0.01$ compared to the H2O control group.

In contrast to a possible hypothesis that GARD, an immunopotentiator, would enhance NV VLP immunogenicity in a powder formulation, GARD did not significantly enhance mucosal or systemic immunity when formulated into the NV dry powder vaccine (FIG. 4, 5, 6). These results are comparable to those observed with an intranasally delivered tetanus dry powder vaccine in which the immunpotentiator, Quillaja saponin, did not enhance mucosal immunity when added to the vaccine formulation containing mucoadhesive components [53]. Possible explanations for the lack of GARD stimulation of the immune response when delivered in a powder could be that the spray drying process may have compromised the TLR7 agonist activity of GARD, or anti-NV immune responses reached a threshold by the nasal NV VLP powder, thus constraining further improvements in immunogenicity of the NV VLPs. To determine if the spray drying process inactivated GARD activity, we stimulated 293XL cells expressing TLR7 with nasal-formulated GARD powder. TLR7 ligation was measured by collecting cell culture supernatants 24 h after stimulation and quantifying IL-8 secretion by ELISA.

Liquid formulations of GARD induced IL-8 secretion in a dose-dependent manner. The powder formulation, which had a GARD content equivalent to 10 μg, induced IL-8 secretion at a level slightly higher than its liquid counterpart, indicating that the TLR7 agonist activity of GARD was retained in the nasal powder formulation. IL-8 was not secreted following stimulation with nasal-formulated NV VLP alone powder, suggesting that the IL-8 secretion elicited by the GARD powder was specifically due to the TLR7 agonist activity of GARD. As further support, whether in a powder or liquid formulation, NV VLPs administered with GARD elicited relatively equal levels of IgG1 and IgG2a antibody titers, indicative of a mixed Th1/Th2 response (See FIGS. 4B, 4C). The shift to a less Th2 predominant response may be due to the effects of GARD, which has previously been shown to induce the secretion of Th1 cytokines both in vitro and in vivo [54, 55]. These results suggest that intranasal immunization with the NV powder vaccine containing the mucoadhesive, the polymer liquid, is sufficient to induce both mucosal and systemic immunity and ameliorates the need for an immunopotentiating agent, unless an IgG2a (Th1) response correlates to a higher level of protection in humans. In this situation a Th1 polarizing immunopotentiator may be required.

Referring now to FIG. 9, fecal and vaginal NV-specific IgA production following intranasal immunization with VLPs in a polymer liquid or PBS liquid. Mouse fecal extracts (9A) and vaginal lavages (9B) were collected on days 0, 12, 21, 42, 56, 84, and 112 and analyzed for NV VLP-specific IgA content by ELISA. Background levels of antigen-specific IgA were not detected (GMT<100) in all pre-immune samples except the following: fecal polymer liquid NV VLP+GARD (2/7 mice); fecal NV VLP alone (1/7 mice); fecal PBS (2/7 mice); and vaginal polymer liquid NV VLP (5/7 mice) (data not shown). Horizontal dashed line indicates the limit of detection for the assay. Error bars represent the standard errors of the mean. ^P<0.05; *P<0.01 compared to the PBS control group.

Figure 10:
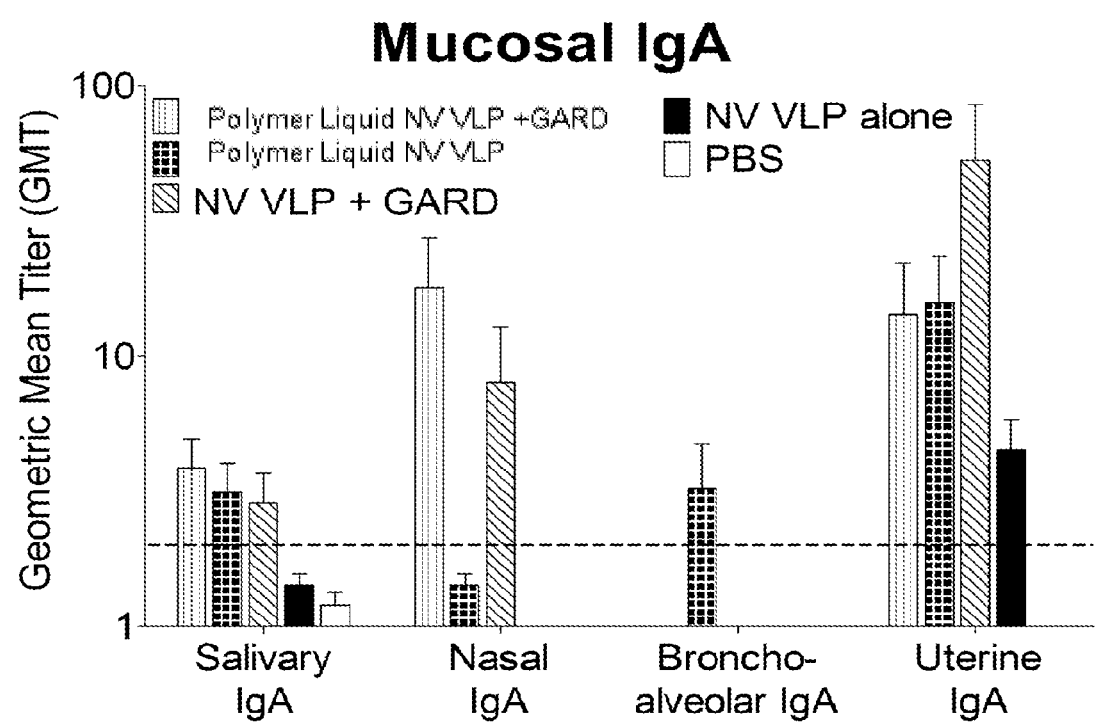

Referring now to FIG. 10, mucosal NV-specific IgA production following intranasal immunization with VLPs in polymer liquid or PBS liquid. Mice were euthanized on day 112. Salivary, nasal, bronchoalveolar, and uterine lavages were collected and analyzed for NV VLP-specific IgA by ELISA. Error bars represent the standard errors of the mean. Horizontal dashed line indicates the limit of detection for the assay. ^P<0.05 compared to the PBS control group.

Figure 9A:
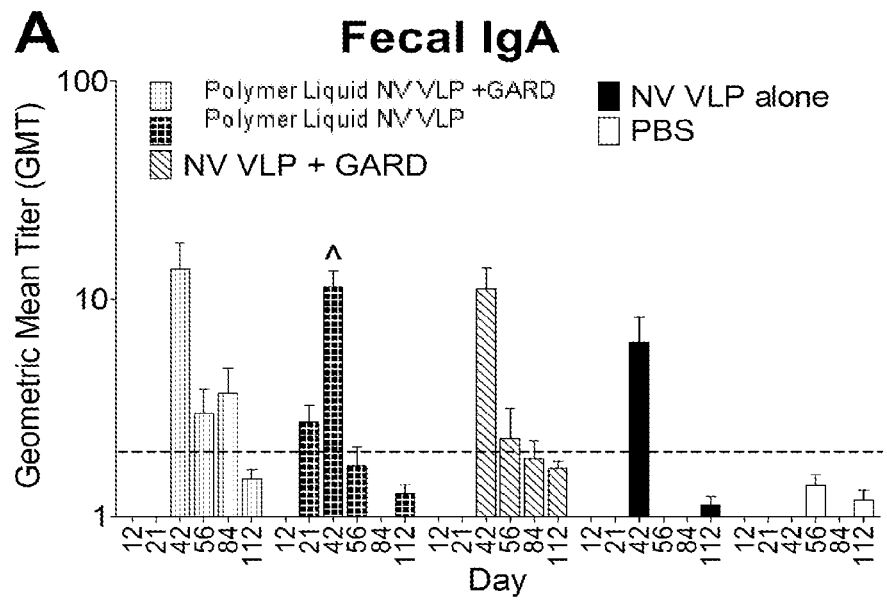

Antigen-specific IgA production was evaluated at other distal mucosal sites of the CMIS. In the gastrointestinal tract, the polymer liquid NV VLP liquid formulation without adjuvant elicited slightly higher fecal and salivary IgA production relative to the liquid formulation without the polymer liquid, but the differences were not statistically significant (P≥0.05) (See FIG. 9A and FIG. 10). The addition of GARD to the polymer liquid NV VLP liquid formulation did not enhance fecal or salivary IgA production relative to the liquid formulation without the polymer liquid or the polymer liquid formulation without adjuvant (FIGS. 9A, 10).

Respiratory Tract (Nasal, Bronchoalveolar).

In the respiratory tract, NV VLPs in the polymer liquid formulation elicited slightly higher nasal and bronchoalveolar IgA production relative to liquid formulations without the polymer liquid, whereas NV VLPs in the polymer liquid formulation with GARD elicited equivalent nasal and broncholaveolar IgA production relative to liquid formulations without the polymer liquid (FIG. 10). When comparing the two polymer-containing liquids, the addition of GARD enhanced nasal IgA production by 13-fold, but did not enhance bronchoalveolar IgA production (FIG. 10).

Reproductive Tract (Vaginal, Uterine).

Figure 9B:
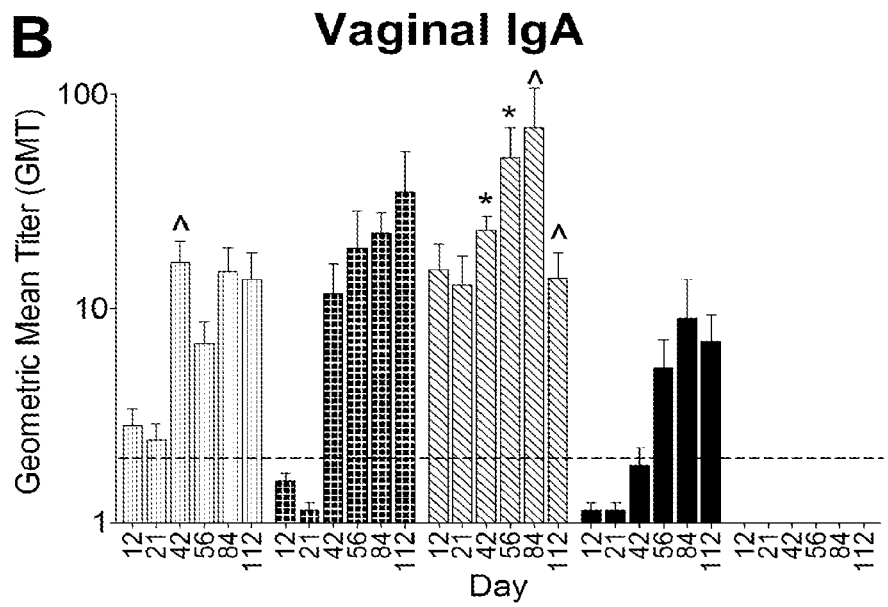

In the female reproductive tract, NV VLPs in the polymer liquid formulation without adjuvant slightly enhanced vaginal and uterine IgA production relative to liquid formulations without the polymer liquid, but the levels were not statistically significant (FIGS. 9B, 10). Surprisingly, the polymer liquid NV VLP liquid formulation with GARD resulted in lower vaginal IgA (days 12, 21, 56, and 84; 5-fold) and uterine IgA (4-fold) production relative to the liquid formulation without the polymer liquid (FIG. 9B, 10). As a result, the polymer liquid NV VLP and GARD liquid formulation elicited nearly equivalent vaginal and uterine IgA levels relative to the polymer liquid NV VLP alone liquid formulation (FIGS. 9, 10).

Prophetic Example 6

Eliciting Robust Immune Response in Human Subjects

A preparation of NoV capsid protein (NoVCP) rVLP is incorporated into liquid formulation of an anionic polysaccharide such as Aloe plant extract and lyophilized. The resulting material is milled under cryogenic conditions and the powder is incorporated into an enterically coated oral formulation, producing a tablet or capsule containing 100 to 1000 μg NoVCP VLP.

The tablet or capsule is then orally administered to a subject to achieve high titers of antibodies in the immunized subject.

Prophetic Example 7

Eliciting Robust Immune Response in Human Subjects

A preparation of human papillomavirus L1 protein rVLP is incorporated into liquid formulation of carboxymethylcellulose (CMC) and lyophilized. The resulting material is milled under cryogenic conditions and the powder is incorporated with other excipients into an enterically coated oral formulation, producing a tablet or capsule.

The tablet or capsule is then administered to a subject producing high titers of antibodies.

The nasal vaccines of the invention also may be prepared using the L1 protein as an antigen. Such a formulation may be prepared substantially as described above for the NoV vaccine.

Materials and Methods

The following methods and materials were used in some of the examples and embodiments described herein.

Preparation of Vaccine Formulations.

Recombinant NV VLPs were expressed in *Nicotiana benthamiana* by Kentucky Bioprocessing (Owensboro, Ky.) following previously described protocols [45]. Clarified leaf extracts were filtered through a 0.2 micron capsule filter and concentrated using a 100 Kd polyethersulfone (PES) tangential flow filtration (TFF) membrane (Pall Corporation, Port Washington, N.Y.). A diethylaminoethyl (DEAE) Sepharose column was used to collect a colorless fraction that allowed recovery of the VLPs in >98% protein purity. Endotoxins and remaining small molecules were removed by Q Column fractionation. The resulting concentrated VLPs as a liquid solution in PBS were diluted to 10 or 25 μg NV VLPs in sterile PBS with or without 10 μg GARD (InvivoGen, San Diego, Calif.).

Polymer liquid formulations were prepared by mixing sterile stock solutions of 0.4% polymer liquid with PBS liquid formulations containing NV VLP with or without GARD at a 1:1 dilution in a biological hood nasal powder formulations (DelSite Biotechnologies, Inc.) were prepared by spray drying the liquid formulations using a Buchi B-290 Mini spray dryer (Buchi laboratories, Switzerland) in a temperature and moisture-controlled class 1000 clean room. The following formulations were prepared: nasal powder alone, NV VLP nasal powder, GARD nasal powder, or NV VLP nasal powder+GARD powder. All nasal powder formulations had a polymer liquid content of 0.25% (w/w). The particle size of the powder formulations was measured using a laser diffraction particle size analyzer (Beckman Coulter LS 230, Brea, Calif.) and the mean particle size was ~20 μm. The powders were transferred to tight-sealed tubes and packaged in moisture and light resistant aluminum foil bags (3M™, Minneapolis, Minn.) with a desiccant pack and stored at room temperature until use.

Nasal Powder NV VLP Structural Characterization.

Light Microscopy.

Micrographs of the nasal powder particles were collected using a Nikon epifluorescent microscope (Nikon, Melville, Ny.). Powder particles were examined either as dry samples, or when rehydrated in simulated nasal fluid as previously described without the addition of bovine serum albumin [46]. Rehydrated particles were stained with 0.01 mg/ml of toluidine blue dye (EMS, Hatfield, Pa.).

Scanning Electron Microscopy.

Dry powder formulations were prepared by dispersing each powder on a metal disk and the particles were held in place using double sided sticky carbon tape. Each powder was sputter coated with gold/palladium for 5 min using a Technis Hummer II sputtering device (Technis, Alexandria, Va.). Micrographs of each powder were collected using a Philips XL30 environmental scanning electron microscope (ESEM).

The Nasal Powder NV VLP Quantification.

NV VLP stability and concentration in the Nasal powder formulations was determined by sucrose gradient sedimentation and ELISA, as described previously [45]. Briefly, a 6-layer gradient was created in Beckman SW55 Ti tubes (Beckman Coulter, Fullerton, Calif.) by layering equal volumes of 60, 50, 40, 30, 20 and 10% sucrose dissolved in modified phosphate buffer (25 mM sodium phosphate, 100 mM NaCl). Following incubation at 4° C. for 2 h, the nasal powder NV VLP, the nasal powder NV VLP+GARD, or insect cell-derived NV VLP standard (Invitrogen, Carlsbad, Calif.) were loaded onto the gradient and centrifuged at 90,000×g for 3 h at 4° C. Fractions were removed from the top to the bottom of the gradient and analyzed by ELISA. Enzyme immunoassay/radioimmunoassay (EIA/RIA) 96-well polystyrene high-binding plates (Corning Inc. Life Sciences, Lowell, Mass.) were precoated with rabbit anti-NV VLP serum for 4 h at room temperature then loaded with the sucrose fractions serially diluted in 1% (wt/vol) dry milk in PBS containing 0.05% Tween-20 (PBS-T) overnight at 4° C. A standard curve was generated with 2-fold dilutions of insect-cell derived NV VLPs at concentrations ranging from 100 to 0.7 ng/ml. The wells were reacted in succession with guinea pig anti-NV VLP serum and goat anti-guinea pig IgG—horseradish peroxidase (HRP) conjugate (Southern Biotech, Birmingham, Ala.), each diluted 1:10,000 in 1% dry milk in PBS-T for 2 h at 37° C. Plates were developed with 4% tetramethylbenzidine (TMB) peroxidase liquid substrate system (KPL Inc., Gaithersburg, Md.) for 2 min then stopped with 1 M phosphoric acid. Absorbance measurements were made at 450 nm using a MRX automatic plate reader (Dynex Technologies, Chantilly, Va.).

Our polymer liquid vaccine studies showed that (in contrast to the NV VLP powder vaccine containing the polymer liquid (FIG. 4, 5, 6)) in most cases, NV VLP liquid vaccines containing the polymer liquid did not significantly enhance systemic or mucosal immune responses relative to liquid formulations without the polymer liquid (FIG. 8, 9, 10). Moreover, the adjuvant effects of the immunopotentiator, GARD, were not observed when delivered in a dry powder formulation with the polymer liquid (FIG. 4, 5, 6), but were observed when delivered in a liquid formulation with the polymer liquid (FIG. 8, 10). Therefore, induction of NV-specific systemic and mucosal immunity was highly affected by the antigen delivery formulation and not by the immunopotentiating properties of the polymer liquid.

All guinea pigs and mice were housed in accordance with United States Department of Agriculture (USDA) and American Association for Laboratory Animal Care (AALAC) standards, provided unlimited access to food and water, and handled in accordance with the Animal Welfare Act and Arizona State University (ASU) Institutional Animal Care and Use Committee (IACUC). Prior to immunization, animals were randomly distributed into vaccination groups and allowed to acclimate for at least one week. Female (250 g) Hartley guinea pigs (Charles River Laboratories International, Inc., Wilmington, Mass.) were distributed into six immunization groups (n=5 per group) and female, 6-week old, BALB/c mice (Charles River Laboratories International, Inc.) were distributed into five immunization groups (n=7 per group; except PBS control group, n=5).

Guinea Pig Immunization.

Guinea pigs were anaesthetized with ketamine (35 mg/kg; Bioniche Pharma USA LLC) and xylazine (5 mg/kg; Akorn, Inc.) administered intraperitoneally prior to immunization. Dry powder vaccines were administered intranasally on days 0 and 21 with 10-12 mg/naris of the nasal powder alone, the nasal powder NV VLP (10 µg), or the nasal powder NV VLP (10 µg)+GARD (10 µg). Comparable liquid formulations of NV VLP (10 µg), NV VLP (10 µg)+GARD (10 µg), or NV VLP (25 µg)+GARD (10 µg) were delivered at a maximum of 5 µl/naris. An intranasal powder delivery device was prepared by fitting a p200 pipette tip with 2 cm of the end removed to 6 cm of rubber tubing attached to a 5 ml syringe (BD Biosciences, Franklin Lakes, N.J.). The p200 pipette tip was used as a connector piece between the syringe and vaccine cartridge. The vaccine cartridge was prepared by cutting a 2 cm piece from the end of a p1000 pipette tip wrapped at the end with parafilm. The narrowest tip of the vaccine cartridge was removed to create wider aperture. One dose of each the nasal powder formulation (10-12 mg/naris) was weighed, loaded into the vaccine cartridge, and subsequently slid into the modified p200 connector tip. A 1.5 cm piece removed from the end of a p1000 pipette tip was fitted onto the vaccine cartridge and used as the point of insertion into the nasal cavity. The modified p1000 nasal tip was coated with KY® jelly lubricant (McNeil-PCC, Inc., Fort Washington, Pa.) and 5 mm of the tip was inserted into the nostril. The Nasal powder vaccine was delivered by administering 2 ml of air from the 5 ml syringe into the nostril and subsequently repeated on the opposite naris. The modified p1000 vaccine cartridge and nasal tips were discarded after each use and the modified p200 connector tip was changed between experimental groups to prevent cross-contamination of vaccine materials.

Mouse Immunization.

Mice were intranasally immunized on days 0 and 21 with NV VLP (25 µg) or NV VLP (25 µg)+GARD (10 µg) in a polymer liquid or PBS liquid formulation. The liquid formulations were administered to conscious mice by gently distributing 5-10 µl of the vaccine dropwise in each naris using a p20 pipette tip. Negative control mice received 10 µl PBS alone.

Sample Collection

Guinea Pig Sample Collection.

Guinea pig serum and vaginal lavage samples were collected prior to the first immunization on day 0 (preimmune) and on days 13, 21, 42, and 60. Serum was isolated by centrifugation of whole blood (150 µl) collected from the lateral saphenous vein of each guinea pig and transferred into heparinized microtubes. Vaginal lavages were collected by lavaging 250 µl of PBS intravaginally with an oral feeding needle (Braintree Scientific Inc., Braintree, Mass.). Fecal pellets were not collected as guinea pigs were group housed. On day 60, guinea pigs were given a pre-anesthetic injection of ketamine (35 mg/kg) and xylazine (5 mg/kg) administered intraperitoneally and then maintained at a surgical plane using isoflurane (2%, Phoenix Pharmaceutical, Inc.) and exsanguinated via cardiocentesis. Distal mucosal samples including salivary, intestinal, nasal, and bronchoalveolar were collected following euthanasia as previously described [4] for mice with some modifications: nasal lavage samples were collected by flushing each naris with 500 μl PBS and bronchoalveolar lavage samples were collected by flushing the lungs with 1 ml PBS. Uterine lavages were collected post-mortem by opening the abdominal cavity, extracting each uterine horn, and flushing each horn with 500 μl PBS. Each horn was excised caudal to the ovary and at the branch where it meets the vagina. All samples were clarified by centrifugation and stored at −80° C. prior to analysis.

Mouse Sample Collection.

Mouse serum, fecal pellets, and vaginal lavage samples were collected on days 0, 12, 21, 42, 56, 84, and 112 as previously described [4]. All mice were humanely euthanized on day 112 in accordance with the Animal Welfare Act and ASU IACUC. Distal mucosal samples including salivary, nasal, and bronchoalveolar were collected following euthanasia as previously described [4]. Uterine lavages were collected post-mortem as described above with 200 μl per uterine horn. All samples were clarified by centrifugation and stored at −80° C. prior to analysis.

NV-Specific ELISAs.

EIA/RIA 96-well polystyrene high-binding plates were coated with 0.5 μg/ml insect cell-derived NV VLPs for 4 h at room temperature then blocked overnight at 4° C. with 10% (fecal and intestinal samples) or 5% (all other samples) dry milk in PBS. Samples were prepared in 2.5% (serum samples) or 5% (mucosal samples) dry milk in PBS-T, serially diluted 2-fold down the microtiter plate, and incubated for 2 h at 37° C. to permit antibody binding as previously described [4, 5, 45]. Briefly, HRP-conjugated anti-guinea pig or anti-mouse antibodies diluted in 2.5% dry milk in PBS-T were loaded onto the wells and incubated for 1 h at 37° C. (see Table 1). Plates were developed with 4% TMB peroxidase liquid substrate system for 5-15 min (depending on the sample). Color development was stopped by the addition of an equal volume of 1 M phosphoric acid and absorbance measurements were made at 450 nm using a MRX automatic plate reader. Endpoint titers are reported as the reciprocal of the highest dilution that had an absorbance value greater than or equal to 0.065 to 0.1 above the background (0.065 for serum and 0.1 for all mucosal samples).

Cell Culture.

Human embryonic kidney (HEK)-293XL cells constitutively expressing human TLR7 (InvivoGen), were cultured in Dulbecco's modified eagle medium (DMEM) (Invitrogen) supplemented with 20% fetal bovine serum (FBS) (Invitrogen), 0.01 mg/ml blasticidin (InvivoGen), and 0.1 mg/ml primocin (InvivoGen) as recommended by the vendor. For stimulation experiments, HEK-293XL cells were cultured in 24-well plates (BD Biosciences) to a density of 1.2×106 cells/well. The nasal powder formulations were resuspended in 200 μl H2O and 100 μl of the suspension was added to the HEK-293XL cells in duplicate wells at a concentration of 25.0 mg/ml (the nasal NV VLP) or 16.5 mg/ml (the nasal GARD). PBS liquid formulations containing GARD were added in duplicate at 1, 2.5, 5, 10, and 25 μg/ml. Following 24 h of stimulation, cell culture supernatants were collected and assayed for IL-8 production by ELISA using the Quantikine Human CXCL8/IL-8 Immunoassay (R&D Systems, Inc., Minneapolis, Minn.). Absorbance measurements made at 450 nm were corrected at 540 nm using a MRX automatic plate reader.

[1] Patel M M, Hall A J, Vinje J, Parashar U D. Noroviruses: a comprehensive review. J Clin Virol 2009 January; 44(1):1-8.

[2] Patel M M, Widdowson M A, Glass R I, Akazawa K, Vinje J, Parashar U D. Systematic literature review of role of noroviruses in sporadic gastroenteritis. Emerg Infect Dis 2008 August; 14(8):1224-31.

[3] Glass R I, Parashar U D, Estes M K. Norovirus gastroenteritis. N Engl J Med 2009 Oct. 29; 361(18):1776-85.

[4] Velasquez L S, Hjelm B E, Arntzen C J, Herbst-Kralovetz M M. An Intranasally Delivered Tlr7 Agonist Elicits Robust Systemic and Mucosal Responses to Norwalk Virus-Like Particles. Clin Vaccine Immunol 2010 Oct. 20.

[5] Guerrero R A, Ball J M, Krater S S, Pacheco S E, Clements J D, Estes M K. Recombinant Norwalk virus-like particles administered intranasally to mice induce systemic and mucosal (fecal and vaginal) immune responses. J Virol 2001 October; 75(20):9713-22.

[6] Mason H S, Ball J M, Shi J J, Jiang X, Estes M K, Arntzen C J. Expression of Norwalk virus capsid protein in transgenic tobacco and potato and its oral immunogenicity in mice. Proc Natl Acad Sci USA 1996 May 28; 93(11):5335-40.

[7] Ball J M, Hardy M E, Atmar R L, Conner M E, Estes M K. Oral immunization with recombinant Norwalk virus-like particles induces a systemic and mucosal immune response in mice. J Virol 1998 February; 72(2):1345-53.

[8] Estes M K, Ball J M, Guerrero R A, Opekun A R, Gilger M A, Pacheco S S, et al. Norwalk virus vaccines: challenges and progress. J Infect Dis 2000 May; 181 Suppl 2:S367-73.

[9] Herbst-Kralovetz M, Mason H S, Chen Q. Norwalk virus-like particles as vaccines. Expert Rev Vaccines 2010 March; 9(3):299-307.

[10] Ball J M, Graham D Y, Opekun A R, Gilger M A, Guerrero R A, Estes M K. Recombinant Norwalk virus-like particles given orally to volunteers: phase I study. Gastroenterology 1999 July; 117(1):40-8.

[11] Tacket C O, Mason H S, Losonsky G, Estes M K, Levine M M, Arntzen C J. Human immune responses to a novel norwalk virus vaccine delivered in transgenic potatoes. J Infect Dis 2000 July; 182(1):302-5.

[12] El-Kamary S S, Pasetti M F, Mendelman P M, Frey S E, Bernstein D I, Treanor J J, et al. Adjuvanted intranasal norwalk virus-like particle vaccine elicits antibodies and antibody-secreting cells that express homing receptors for mucosal and peripheral lymphoid tissues. J Infect Dis 2010 Dec. 1; 202(11): 1649-58.

[13] Green K Y, Lew J F, Jiang X, Kapikian A Z, Estes M K. Comparison of the reactivities of baculovirus-expressed recombinant Norwalk virus capsid antigen with those of the native Norwalk virus antigen in serologic assays and some epidemiologic observations. J Clin Microbiol 1993 August; 31(8):2185-91.

[14] Reeck A, Kavanagh O, Estes M K, Opekun A R, Gilger M A, Graham D Y, et al. Serological correlate of protection against norovirus-induced gastroenteritis. J Infect Dis 2010 Oct. 15; 202(8): 1212-8.

[15] van Ginkel F W, Nguyen H H, McGhee J R. Vaccines for mucosal immunity to combat emerging infectious diseases. Emerg Infect Dis 2000 March-April; 6(2):123-32.

[16] Holmgren J, Czerkinsky C. Mucosal immunity and vaccines. Nat Med 2005 April; 11(4 Suppl):S45-53.

[17] Holmgren J, Harandi A M, Czerkinsky C. Mucosal adjuvants and anti-infection and anti-immunopathology vaccines based on cholera toxin, cholera toxin B subunit and CpG DNA. Expert Rev Vaccines 2003 April; 2(2): 205-17.

[18] Yuki Y, Kiyono H. Mucosal vaccines: novel advances in technology and delivery. Expert Rev Vaccines 2009 August; 8(8):1083-97.

[19] Chadwick S, Kriegel C, Amiji M. Delivery strategies to enhance mucosal vaccination. Expert Opin Biol Ther 2009 April; 9(4):427-40.

[20] Kuolee R, Chen W. M cell-targeted delivery of vaccines and therapeutics. Expert Opin Drug Deliv 2008 June; 5(6):693-702.

[21] Graham B S, Kines R C, Corbett K S, Nicewonger J, Johnson T R, Chen M, et al. Mucosal delivery of human papillomavirus pseudovirus-encapsidated plasmids improves the potency of DNA vaccination. Mucosal Immunol 2010 Jun. 16; 3(5):475-86.

[22] Inskeep T K, Stahl C, Odle J, Oakes J, Hudson L, Bost K L, et al. Oral vaccine formulations stimulate mucosal and systemic antibody responses against staphylococcal enterotoxin B using a piglet model. Clin Vaccine Immunol 2010 Jun. 16; 18(8):1163-9.

[23] Fraillery D, Zosso N, Nardelli-Haefliger D. Rectal and vaginal immunization of mice with human papillomavirus L1 virus-like particles. Vaccine 2009 Apr. 14; 27(17): 2326-34.

[24] Noda K, Kodama S, Umemoto S, Abe N, Hirano T, Suzuki M. Nasal vaccination with P6 outer membrane protein and alpha-galactosylceramide induces nontypeable Haemophilus influenzae-specific protective immunity associated with NKT cell activation and dendritic cell expansion in nasopharynx. Vaccine 2010 May 14; 28(31): 5068-74.

[25] Hefferon K L. The Mucosal Immune Response to Plant-Derived Vaccines. Pharm Res 2010 May 14; 27(10): 2040-2.

[26] Lanza S R, Menin A, Ertl H C, Bafica A, Pinto A R. Simian recombinant adenovirus delivered by the mucosal route modulates gammadelta T cells from murine genital tract. Vaccine 2010 Jun. 23; 28(29):4600-8.

[27] Huang J, Garmise R I, Crowder T M, Mar K, Hwang C R, Hickey A J, et al. A novel dry powder influenza vaccine and intranasal delivery technology: induction of systemic and mucosal immune responses in rats. Vaccine 2004 Dec. 21; 23(6):794-801.

[28] Garmise R J, Staats H F, Hickey A J. Novel dry powder preparations of whole inactivated influenza virus for nasal vaccination. AAPS PharmSciTech 2007; 8(4):E81.

[29] Turker S, Onur E, Ozer Y. Nasal route and drug delivery systems. Pharm World Sci 2004 June; 26(3): 137-42.

[30] Jiang L, Gao L, Wang X, Tang L, Ma J. The application of mucoadhesive polymers in nasal drug delivery. Drug Dev Ind Pharm 2010 March; 36(3):323-36.

[31] Mestecky J. The common mucosal immune system and current strategies for induction of immune responses in external secretions. J Clin Immunol 1987 July; 7(4):265-76.

[32] Hickey A J, Garmise R J. Dry powder nasal vaccines as an alternative to needle-based delivery. Crit Rev Ther Drug Carrier Syst 2009; 26(1):1-27.

[33] Treanor J J, Kotloff K, Betts R F, Belshe R, Newman F, Iacuzio D, et al. Evaluation of trivalent, live, cold-adapted (CAIV-T) and inactivated (TIV) influenza vaccines in prevention of virus infection and illness following challenge of adults with wild-type influenza A (H1N1), A (H3N2), and B viruses. Vaccine 1999 Dec. 10; 18(9-10): 899-906.

[34] Nichol K L, Mendelman P M, Mallon K P, Jackson L A, Gorse G J, Belshe R B, et al. Effectiveness of live, attenuated intranasal influenza virus vaccine in healthy, working adults: a randomized controlled trial. JAMA 1999 Jul. 14; 282(2):137-44.

[35] Belshe R B, Mendelman P M, Treanor J, King J, Gruber W C, Piedra P, et al. The efficacy of live attenuated, cold-adapted, trivalent, intranasal influenzavirus vaccine in children. N Engl J Med 1998 May 14; 338(20):1405-12.

[36] Davis S S. Nasal vaccines. Adv Drug Deliv Rev 2001 September 23; 51(1-3):21-42.

[37] Buonaguro L, Visciano M L, Tornesello M L, Tagliamonte M, Biryahwaho B, Buonaguro F M. Induction of systemic and mucosal cross-clade neutralizing antibodies in BALB/c mice immunized with human immunodeficiency virus type 1 clade A virus-like particles administered by different routes of inoculation. J Virol 2005 June; 79(11):7059-67.

[38] Balmelli C, Roden R, Potts A, Schiller J, De Grandi P, Nardelli-Haefliger D. Nasal immunization of mice with human papillomavirus type 16 virus-like particles elicits neutralizing antibodies in mucosal secretions. J Virol 1998 October; 72(10):8220-9.

[39] Nardelli-Haefliger D, Roden R, Balmelli C, Potts A, Schiller J, De Grandi P. Mucosal but not parenteral immunization with purified human papillomavirus type 16 virus-like particles induces neutralizing titers of antibodies throughout the estrous cycle of mice. J Virol 1999 November; 73(11):9609-13.

[40] Canessa C, Vierucci S, Azzari C, Vierucci A. The immunity of upper airways. Int J Inunnunopathol Pharmacol 2010 January-March; 23(1 Suppl):8-12.

[41] Garg N K, Mangal S, Khambete H, Sharma P K, Tyagi R K. Mucosal delivery of vaccines: role of mucoadhesive/biodegradable polymers. Recent Pat Drug Deliv Formul 2010 Jun. 1; 4(2):114-28.

[42] Pawar D, Goyal A K, Mangal S, Mishra N, Vaidya B, Tiwari S, et al. Evaluation of mucoadhesive PLGA microparticles for nasal immunization. AAPS J 2010 June; 12(2):130-7.

[43] Ni YaY, K. M., inventor In Situ Gel Formation of Pectin. U.S. Pat. No. 6,777,000 B2. 2004.

[44] Ni YaY, K. M., inventor Delivery of physiological agents with in-situ gels comprising anionic polysaccharides. U.S. Pat. No. 7,494,669. 2009.

[45] Santi L, Batchelor L, Huang Z, Hj elm B, Kilbourne J, Arntzen C J, et al. An efficient plant viral expression system generating orally immunogenic Norwalk virus-like particles. Vaccine 2008 Mar. 28; 26(15): 1846-54.

[46] Lorin M I, Gaerlan P F, Mandel I D. Quantitative composition of nasal secretions in normal subjects. J Lab Clin Med 1972 August; 80(2):275-81.

[47] Huang Z, Elkin G, Maloney B J, Beuhner N, Arntzen C J, Thanavala Y, et al. Virus-like particle expression and assembly in plants: hepatitis B and Norwalk viruses. Vaccine 2005 Mar. 7; 23(15):1851-8.

[48] Saluja V, Amorij J P, Kapteyn J C, de Boer A H, Frijlink H W, Hinrichs W L. A comparison between spray drying and spray freeze drying to produce an influenza subunit vaccine powder for inhalation. J Control Release 2010 Jun. 1; 144(2):127-33.

[49] Alpar H O, Somavarapu S, Atuah K N, Bramwell V W. Biodegradable mucoadhesive particulates for nasal and pulmonary antigen and DNA delivery. Adv Drug Deliv Rev 2005 Jan. 10; 57(3):411-30.

[50] Bernstein D I, Harrison C J, Tomai M A, Miller R L. Daily or weekly therapy with resiquimod (R-848) reduces genital recurrences in herpes simplex virus-infected guinea pigs during and after treatment. J Infect Dis 2001 Mar. 15; 183(6):844-9.

[51] Bernstein D I, Harrison C J, Tepe E R, Shahwan A, Miller R L. Effect of imiquimod as an adjuvant for immunotherapy of genital HSV in guinea-pigs. Vaccine 1995 January; 13(1):72-6.

[52] Wimer-Mackin S, Hinchcliffe M, Petrie C R, Warwood S J, Tino W T, Williams M S, et al. An intranasal vaccine targeting both the Bacillus anthracis toxin and bacterium provides protection against aerosol spore challenge in rabbits. Vaccine 2006 May 1; 24(18):3953-63.

[53] Tafaghodi M, Rastegar S. Preparation and in vivo study of dry powder microspheres for nasal immunization. J Drug Target 2010 April; 18(3):235-42.

[54] Baldwin S L, Bertholet S, Kahn M, Zharkikh I, Ireton G C, Vedvick T S, et al. Intradermal immunization improves protective efficacy of a novel TB vaccine candidate. Vaccine 2009 May 18; 27(23):3063-71.

[55] Ma Y, Poisson L, Sanchez-Schmitz G, Pawar S, Qu C, Randolph G J, et al. Assessing the immunopotency of Toll-like receptor agonists in an in vitro tissue-engineered inununological model. Immunology 2010 July; 130(3): 374-87.

What is claimed is:

1. A method of producing an immune response in a subject, comprising the steps of:
   (i) preparing a dry powder immunogenic composition, wherein said composition consists of:
      a) viral protein subunits which can assemble into virus-like particles consisting of a norovirus capsid protein (NoVCP); and
      b) an anionic polysaccharide extracted from an aloe vera plant, wherein said VLPs are stabilized by the anionic polysaccharide at a pH over 6.5, and wherein the anionic polysaccharide has characteristics including a degree of methylation of 10% or less, a molecular weight $>1\times10^6$ Daltons, an intrinsic viscosity from about 550 ml/g to about 978 ml/g, when dissolved in 0.1 M NaCl at a concentration of 0.0005-0.2% (w/v), a galacturonic acid content of at least 70%, a rhamnose content from about 2 to about 15% by mole, and capable of calcium gel formation when present at a concentration of 0.2% (w/v) in an aqueous solution comprising 2 mM calcium chloride; and
   (ii) intranasally inoculating the subject with the dry powder immunogenic composition to elicit an immune response, where said dry powder immunogenic composition does not include an adjuvant in addition to the anionic polysaccharide.

2. The method of claim 1, wherein the norovirus is selected from the group consisting of norovirus genogroup I, norovirus genogroup II, norovirus genogroup III or norovirus genogroup IV.

3. The method of claim 1, wherein said dry powder immunogenic composition does not include TLR agonists.

4. The method of claim 1, wherein the polysaccharide may comprise low methoxy-pectin, Xanthan, carboxymethylcellulose, or a combination thereof.

5. The method of claim 1, wherein said dry powder formulation forms a gel upon delivery to the nasal passage, wherein said polysaccharide in said formulation is sodium polygalacturonate having a galacturonic acid (Gal UA) content of >90%, a degree of methylation of <10%, and a molecular weight of >400 kDa weight average.

6. The method of claim 1, wherein said polysaccharide is sodium polygalacturonate.

\* \* \* \* \*